US010478346B2

(12) United States Patent
Knutson

(10) Patent No.: US 10,478,346 B2
(45) Date of Patent: Nov. 19, 2019

(54) METHODS OF HANDLING ADHESIVE LAMINATE PATCHES

(71) Applicant: 3M INNOVATIVE PROPERTIES COMPANY, Saint Paul, MN (US)

(72) Inventor: Gordon P. Knutson, Beldenville, WI (US)

(73) Assignee: 3M Innovative Properties Company, St. Paul, MN (US)

(*) Notice: Subject to any disclaimer, the term of this patent is extended or adjusted under 35 U.S.C. 154(b) by 362 days.

(21) Appl. No.: 15/534,081

(22) PCT Filed: Dec. 8, 2015

(86) PCT No.: PCT/US2015/064364
§ 371 (c)(1),
(2) Date: Jun. 8, 2017

(87) PCT Pub. No.: WO2016/099986
PCT Pub. Date: Jun. 23, 2016

(65) Prior Publication Data

US 2018/0369023 A1 Dec. 27, 2018

Related U.S. Application Data

(60) Provisional application No. 62/093,440, filed on Dec. 18, 2014.

(51) Int. Cl.
*B29C 65/48* (2006.01)
*B29C 65/78* (2006.01)
(Continued)

(52) U.S. Cl.
CPC .. *A61F 13/15756* (2013.01); *A61F 13/00029* (2013.01); *A61F 13/00063* (2013.01);
(Continued)

(58) Field of Classification Search
CPC .............. A61F 13/0276; A61F 13/0279; A61F 13/0296; A61F 13/15756; A61F 2013/008;
(Continued)

(56) References Cited

U.S. PATENT DOCUMENTS

| | | |
|---|---|---|
| 4,693,776 A | 9/1987 | Krampe |
| 4,834,979 A | 5/1989 | Gale |

(Continued)

FOREIGN PATENT DOCUMENTS

| | | |
|---|---|---|
| WO | WO 98/31307 | 7/1998 |
| WO | WO 2006-135696 | 12/2006 |

OTHER PUBLICATIONS

International Search Report for PCT International Application No. PCT/US2015/064364, dated Feb. 23, 2016, 3 pages.

*Primary Examiner* — Philip C Tucker
*Assistant Examiner* — Brian R Slawski
(74) *Attorney, Agent, or Firm* — Eric E. Silverman

(57) ABSTRACT

Methods of handling adhesive laminate patches. A first article, passed over a first supporting structure, includes disconnected adhesive laminate patches adhered to a first web, each patch being aligned over and adhered to a tab. A second web can be passed over a second supporting structure that is separated from the first supporting structure by a gap. The first article can be passed over the first supporting structure to lift a leading portion of a first tab and a first patch off of the first web together, such that the first tab facilitates transfer of the first patch across the gap. The first patch can then be adhered to the second web; and the second web can be advanced to transfer the first patch, and first tab, onto the second web to form a second article comprising patches aligned over tabs on the second web.

15 Claims, 11 Drawing Sheets

(51) Int. Cl.

| | |
|---|---|
| ***B29C 65/00*** | (2006.01) |
| ***B32B 37/00*** | (2006.01) |
| ***B32B 38/10*** | (2006.01) |
| ***B32B 38/18*** | (2006.01) |
| ***B32B 7/06*** | (2019.01) |
| ***A61F 13/15*** | (2006.01) |
| ***A61L 15/58*** | (2006.01) |
| ***A61F 13/00*** | (2006.01) |
| ***A61F 13/02*** | (2006.01) |
| ***A61K 9/70*** | (2006.01) |
| *B32B 38/12* | (2006.01) |

(52) U.S. Cl.
CPC ...... *A61F 13/0276* (2013.01); *A61F 13/0289* (2013.01); *A61K 9/7038* (2013.01); *A61L 15/58* (2013.01); *A61F 2013/008* (2013.01); *A61F 2013/00817* (2013.01); *B29C 65/4825* (2013.01); *B29C 65/7858* (2013.01); *B29C 66/45* (2013.01); *B29C 66/472* (2013.01); *B29C 66/80* (2013.01); *B32B 7/06* (2013.01); *B32B 37/025* (2013.01); *B32B 38/10* (2013.01); *B32B 38/12* (2013.01)

(58) Field of Classification Search
CPC .......... A61F 2013/00817; A61K 9/703; A61K 9/7038; A61K 9/7084; A61L 15/58; B29C 2793/0036; B29C 2793/0054; B29C 65/00; B29C 65/48; B29C 65/4825; B29C 65/78; B29C 65/7858; B29C 65/7888; B29C 65/7894; B29C 66/00; B29C 66/40; B29C 66/41; B29C 66/45; B29C 66/47; B29C 66/472; B29C 66/80; B29C 66/84; B32B 37/02; B32B 37/025; B32B 37/12; B32B 38/10; B32B 38/18; B32B 7/06
USPC ......... 156/60, 152, 184, 185, 187, 191, 192, 156/193, 230, 234, 235, 238, 239, 247, 156/248, 249, 250, 256, 257, 259, 264, 156/265, 268, 269, 271, 289, 297, 299, 156/324
See application file for complete search history.

(56) References Cited

U.S. PATENT DOCUMENTS

| | | | |
|---|---|---|---|
| 5,223,261 | A | 6/1993 | Nelson |
| 5,380,760 | A | 1/1995 | Wendel |
| 5,656,286 | A | 8/1997 | Miranda |
| 5,783,269 | A | 6/1998 | Heilmann |
| 5,891,290 | A | 4/1999 | Deurer |
| 6,004,578 | A | 12/1999 | Lee |
| 6,024,976 | A | 2/2000 | Miranda |
| 6,059,913 | A | 5/2000 | Asmussen |
| 6,129,929 | A | 10/2000 | Wick |
| 6,149,935 | A | 11/2000 | Chiang |
| 6,315,854 | B1 | 11/2001 | Anhauser |
| 6,365,178 | B1 | 4/2002 | Venkateshwaran |
| 6,464,818 | B1 | 10/2002 | Schulze |
| 6,571,983 | B1 | 6/2003 | Schumann |
| 6,786,266 | B2 | 9/2004 | Fukada |
| 7,029,549 | B1 | 4/2006 | Von Falkenhausen |
| 7,506,760 | B2 | 3/2009 | Grossman |
| 8,071,126 | B2 | 12/2011 | Sekiguchi |
| 8,287,899 | B2 | 10/2012 | Dupont |
| 8,608,889 | B2 | 12/2013 | Sever |
| 2002/0124948 | A1 | 9/2002 | Mikkelsen |
| 2003/0204158 | A1* | 10/2003 | Johnson .............. A61F 13/0276 602/41 |
| 2004/0219195 | A1 | 11/2004 | Hart |
| 2006/0151347 | A1* | 7/2006 | Grossman ............. A61F 15/001 206/440 |
| 2008/0202675 | A1 | 8/2008 | Sever |
| 2010/0247613 | A1 | 9/2010 | Holmes |
| 2012/0057287 | A1 | 3/2012 | Chaves |
| 2012/0205037 | A1 | 8/2012 | Kitzer |
| 2014/0066866 | A1 | 3/2014 | Sever |
| 2014/0243788 | A1 | 8/2014 | Cantor |
| 2014/0303574 | A1 | 10/2014 | Knutson |

* cited by examiner

METHODS OF HANDLING ADHESIVE LAMINATE PATCHES

CROSS REFERENCE TO RELATED APPLICATIONS

This application is a national stage filing under 35 U.S.C. 371 of PCT/US2015/064364, filed Dec. 8, 2015, which claims the benefit of U.S. Provisional Patent Application No. 62/093,440, filed Dec. 18, 2014, the disclosure of which are incorporated by reference in their entirety herein.

FIELD

The present disclosure generally relates to a method of handling adhesive laminates, particularly, a method of handling adhesive laminate patches, and more particularly, a method of handling adhesive laminate patches using integral applicator tabs.

BACKGROUND

Adhesive laminate sections, or patches, can be used for a variety of purposes, including wound protection and/or treatment, continuous transdermal administration of an active ingredient (e.g., a drug), or combinations thereof.

In general, an adhesive patch comprises a support or backing that can be made of a cloth, a plastic film, or the like, and an adhesive layer laminated on the backing. The adhesive patch is generally provided with a release liner laminated on the adhesive layer and packaged in a package (e.g., made of a resin film).

Adhesive patches are often prepared by stamping or cutting the patches from a larger master roll or "jumbo" that is many times longer and may also be wider than an individual patch. This process of forming a master roll may be more convenient and efficient than trying to produce many individual patches on a piece-by-piece basis, but the subsequent stamping or cutting process generally results in production of waste material. The amount of waste material and the degree of undesirability of such waste will vary depending on the type of material and the nature of the patches that are created.

As an example, transdermal drug delivery devices often consist of a drug containing adhesive patch, a so-called "drug-in-adhesive" patch. The adhesive is placed in contact with a skin surface when in use and the drug passes from the device into the skin. Such devices typically have a release liner that protects the adhesive during storage and which is typically removed just before application of the device to the skin. In some instances it is desirable to use a release liner with a larger surface area than the adhesive portion of the device, as this may make the device easier to handle by a patient and/or may improve the storage stability of the device. Such devices are often referred to as having an extended release liner.

A typical production process for transdermal drug delivery devices in which a master roll is formed and subsequently converted by stamping or cutting individual devices for subsequent packaging and distribution to a patient leaves waste with the same composition as the devices (i.e., containing drug) that must be disposed. Production of devices having an extended liner requires additional converting steps and generates additional waste material.

SUMMARY

It would be desirable to produce adhesive laminate sections, or patches, from a master roll using a converting process that reduces or eliminates production waste. It would also be desirable to produce patches (e.g., medical articles, such as transdermal drug delivery devices) using a converting process that reduces or eliminates the production of drug-containing waste. It would be further desirable to efficiently produce adhesive patches having an integral applicator tab that can aid in applying the patch to skin. Such an applicator tab can be formed during and used in methods of the present disclosure to efficiently produce adhesive patch assemblies comprising a patch on an extended release liner.

Some aspects of the present disclosure include a method of handling adhesive laminate patches. The method can include providing a first article comprising a plurality of disconnected adhesive laminate patches adhered to a first web, wherein each patch is aligned over and adhered to a tab in the first web, such that a leading edge of each tab is located adjacent a leading edge of each patch. The method can further include providing a first supporting structure and a second supporting structure positioned adjacent the first supporting structure, wherein the second supporting structure and the first supporting structure are separated by a gap. The method can further include leading a second web over the second supporting structure, wherein the second web has a release surface, and wherein the second web is oriented such that the release surface of the second web faces the first supporting structure. The method can further include passing the first article over the first supporting structure to cause a leading portion of a first tab and a leading portion of a first patch aligned over the first tab to lift off of the first web together in such a way that the leading portion of the first patch is supported by the first tab and extends across the gap between the first supporting structure and the second supporting structure. The method can further include adhering the leading portion of the first patch to the second web on the second supporting structure; and advancing the second web on the second supporting structure to transfer the first patch from the first web to the second web to form a second article comprising a plurality of patches aligned over tabs on the second web, wherein the patches are spaced apart longitudinally on the second web.

Other features and aspects of the present disclosure will become apparent by consideration of the detailed description and accompanying drawings.

DETAILED DESCRIPTION

Figure 1:
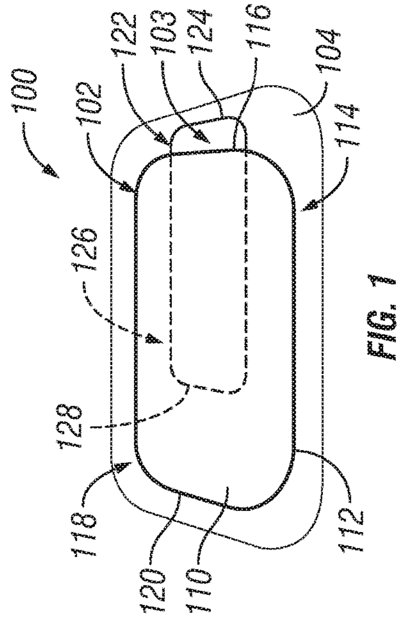
FIG. 1 is a perspective view of adhesive patch assembly according to one embodiment of the present disclosure, the adhesive patch assembly including an adhesive patch, a tab, and a release liner.

The present disclosure generally relates to methods for handling an adhesive laminate, and particularly, to methods for handling adhesive laminate patches (or simply "adhesive patches") using integral applicator tabs that form a portion of the resulting adhesive patch assembly or article. The tab can be used to facilitate applying the adhesive patch, e.g., to skin, and can also be used during the method of making the adhesive patch and adhesive patch assembly to enhance handling of the adhesive patch. Particularly, the tab can be provided in a first web to which the adhesive patch is applied and can facilitate the transfer of the adhesive patch from the first web to a second downstream web. For example, in some embodiments, the tab can be die-cut in a first release liner of the adhesive laminate and can then be used to transfer die-cut patches from the first release liner to a second release liner. The tab can remain with an adhesive patch and form a portion of the resulting adhesive patch assembly, and can further be used as an application aid when the adhesive patch is applied, e.g., to skin.

Methods of the present disclosure allow adhesive patches to be die-cut in a tight, efficient pattern and spread in a cross-machine (or cross-web) direction and/or a machine direction (MD) for converting final adhesive patch configuration in a different, more widespread pattern.

Definitions

The term "a", "an", and "the" are used interchangeably with "at least one" to mean one or more of the elements being described.

The term "and/or" means either or both. For example "A and/or B" means only A, only B, or both A and B.

The terms "including," "comprising," or "having," and variations thereof, are meant to encompass the items listed thereafter and equivalents thereof as well as additional items.

Unless specified or limited otherwise, the terms "supported," and "coupled" and variations thereof are used broadly and encompass both direct and indirect supports, and couplings.

The terms "polymer" and "polymeric material" refer to both materials prepared from one monomer such as a homopolymer or to materials prepared from two or more monomers such as a copolymer, terpolymer, or the like. Likewise, the term "polymerize" refers to the process of making a polymeric material that can be a homopolymer, copolymer, terpolymer, or the like. The terms "copolymer" and "copolymeric material" refer to a polymeric material prepared from at least two monomers.

The terms "room temperature" and "ambient temperature" are used interchangeably to mean a temperature in the range of 20° C. to 25° C.

The term "flexible" can generally be used to refer to a material that is drapable. That is, a section of material 5 cm×15 cm when held upright (long end up) folds over under its own weight to drop the opposite end to or below the holder, when performed at ambient conditions. The term "rigid" can generally be used to refer to a material that is essentially non-drapable. That is, a section of material 5 cm×15 cm when held upright (long end up) stands straight up with little or no deflection, when performed at ambient conditions. In some embodiments, rigid materials can show less than 20 degrees of deflection from vertical. "Semi-rigid" materials can be those that exhibit more than 20 degrees of deflection but whose opposite end does not drop below the holder.

The term "transparent" and variations thereof, is used to refer to a material that, when applied to a patient (e.g., at a wound site), the area underlying the material can be sufficiently visualized through the material to permit visual inspection or observation of the area (e.g., wound) by a health care worker.

FIG. 1 illustrates an adhesive patch assembly 100 according to one embodiment of the present disclosure. The adhesive patch assembly 100 includes an adhesive laminate patch (also sometimes referred to as "adhesive patch" or "patch") 102, a tab (also sometimes referred to as an "integral tab," an "applicator tab," or an "integral applicator tab") 103, and a release liner 104. The release liner 104 is shown as extending beyond the edge or periphery of the patch 102 on all sides, such that the release liner 104 of FIG. 1 is an extended release liner. In some embodiments, the patch 102 and/or the tab 103 can be transparent.

In some embodiments, the adhesive patch 102 can include a transdermal drug delivery patch comprising a drug that can be administered via skin, particularly, mammalian skin, and particularly transdermally.

The adhesive laminate from which the patch 102 is formed is generally characterized as a two or more layer structure having an adhesive layer (or simply "adhesive") 112 and a backing layer (or simply "backing") 110. The backing layer 110 can be described as having a first major surface and a second major surface opposite the first major surface, and the adhesive layer 112 can be provided on the second major surface of the backing layer 110.

The adhesive layer 112 may be continuous or discontinuous, but is preferably continuous. The backing 110 is generally continuous, although it may be perforated or otherwise have gaps. In some embodiments, the adhesive and backing layers 112 and 110 are both continuous.

The adhesive layer 112 will generally be selected according to the desired end use of the articles prepared by the present method. Examples of suitable adhesives include acrylates, silicones, polyisobutylenes, synthetic rubber, natural rubber, and copolymers and mixtures thereof. Further description of suitable adhesives may be found in U.S. Pat. No. 5,656,286 (Miranda et al.), U.S. Pat. No. 4,693,776 (Krampe et al.), U.S. Pat. No. 5,223,261 (Nelson et al.), and U.S. Pat. No. 5,380,760 (Wendel et al.) the disclosures of which are incorporated herein by reference.

Typical examples of flexible films employed as conventional tape backings which may be useful as a backing layer 110 include those made from polymer films such as polypropylene; polyethylene, particularly low density polyethylene, linear low density polyethylene, metallocene polyethylenes, and high density polyethylene; polyvinyl chloride; polyester (e.g., polyethylene terephthalate); polyvinylidene chloride; ethylene-vinyl acetate (EVA) copolymer; polyurethane; cellulose acetate; and ethyl cellulose. Coextruded multilayer polymeric films are also suitable, such as those described in U.S. Pat. No. 5,783,269 (Heilmann et al.), the disclosure of which is incorporated herein by reference. Backings that are layered such as polyethylene terephthalate-aluminum-polyethylene composites and polyethylene terephthalate-EVA composites are also suitable. Foam tape backings, such as closed cell polyolefin films used in 3M™ 1777 Foam Tape and 3M™ 1779 Foam Tape are also suitable. Polyethylenes, polyethylene blends, and polypropylenes are preferred polymer films. Polyethylenes and polyethylene blends are most preferred polymer films.

In some embodiments, the backing layer 110 is transparent. Additives may also be added to the backing layer 110, such as tackifiers, plasticizers, colorants, and anti-oxidants. It may be desirable to use a flexible backing layer, particularly for medical or pharmaceutical applications where the end use product is adhered to skin. In some embodiments, the methods of the present disclosure find particular utility for island placement converting of adhesive laminates having very flexible backings, such as thin polyethylene backings, which are generally difficult to handle in small, individual patch shaped sections.

In some embodiments, the backing layer thickness is at least 0.01 mm (10 μm); in some embodiments, at least 0.02 mm (20 μm); in some embodiments, at least 0.025 mm (25 μm); and in some embodiments, at least 0.04 mm (40 μm). In some embodiments, the backing layer thickness is no greater than 1 mm; in some embodiments, no greater than 0.5 mm (500 μm); in some embodiments, no greater than 0.2 mm (200 μm); in some embodiments, no greater than 0.15 mm (150 μm); in some embodiments, no greater than 0.1 mm (100 μm); in some embodiments, no greater than 0.08 mm (80 μm); and in some embodiments, no greater than 0.05 mm (50 μm).

As shown in FIG. 1, the patch 102 can include a leading portion 114 comprising a leading edge 116 (e.g., in a machine or web direction) and a trailing portion 118 comprising a trailing edge 120. Similarly, the tab 103 can include a leading portion 122 comprising a leading edge 124 and a trailing portion 126 comprising a trailing edge 128. The leading edge 124 of the tab 103 is generally located adjacent the leading edge 116 of the patch 102.

In the embodiment illustrated in FIG. 1, the leading edge 124 of the tab 103 extends beyond the leading edge 116 of the patch 102, i.e., at least a portion of the leading edge 124 is positioned downstream (or downweb) of at least a portion of the leading edge 116 of the patch 102. Such a configuration can allow the leading portion 122 of the tab 103 to be grasped by a user to facilitate removal of the patch 102 from the release liner 104, and can also allow the leading portion 122 of the tab 103 to be extended across a gap between adjacent supporting structures in a web handling apparatus during a web handling method of the present disclosure to facilitate transferring the patch 102 from a first web to a second web, e.g., to island place the patch 102 on the second web, as described in greater detail with respect to FIGS. 2 and 3A-3L.

However, the leading edge 124 of the tab 103 need not extend beyond the leading edge 116 of the patch 102. Rather, in some embodiments, at least a portion of the leading edge 124 of the tab 103 can be at the same location as, or overlap, at least a portion of the leading edge 116 of the patch 102. Still, in some embodiments, the leading edge 124 of the tab 103 may be slightly inside or internal with respect to the leading edge 116 of the patch 102, such that at least a portion of the leading edge 124 is positioned upstream (or upweb) of at least a portion of the leading edge 116 of the patch 102.

That is, in order for the leading edge 124 of the tab 103 to be positioned "adjacent" the leading edge 116 of the patch 102, at least a portion of the leading edge 124 of the tab 103 is positioned slightly upstream of, slightly downstream of, or at the same web direction location as the leading edge 116 of the patch 102, and particularly, is located relative to the leading edge 116 of the patch 102, such that the tab 103 facilitates patch transfer during web handling processes and/or application of the patch 102.

The tab 103 is generally rigid or semi-rigid, and particularly, is rigid relative to (i.e., more rigid than) the flexible adhesive laminate from which the patch 102 is formed.

Figure 2:
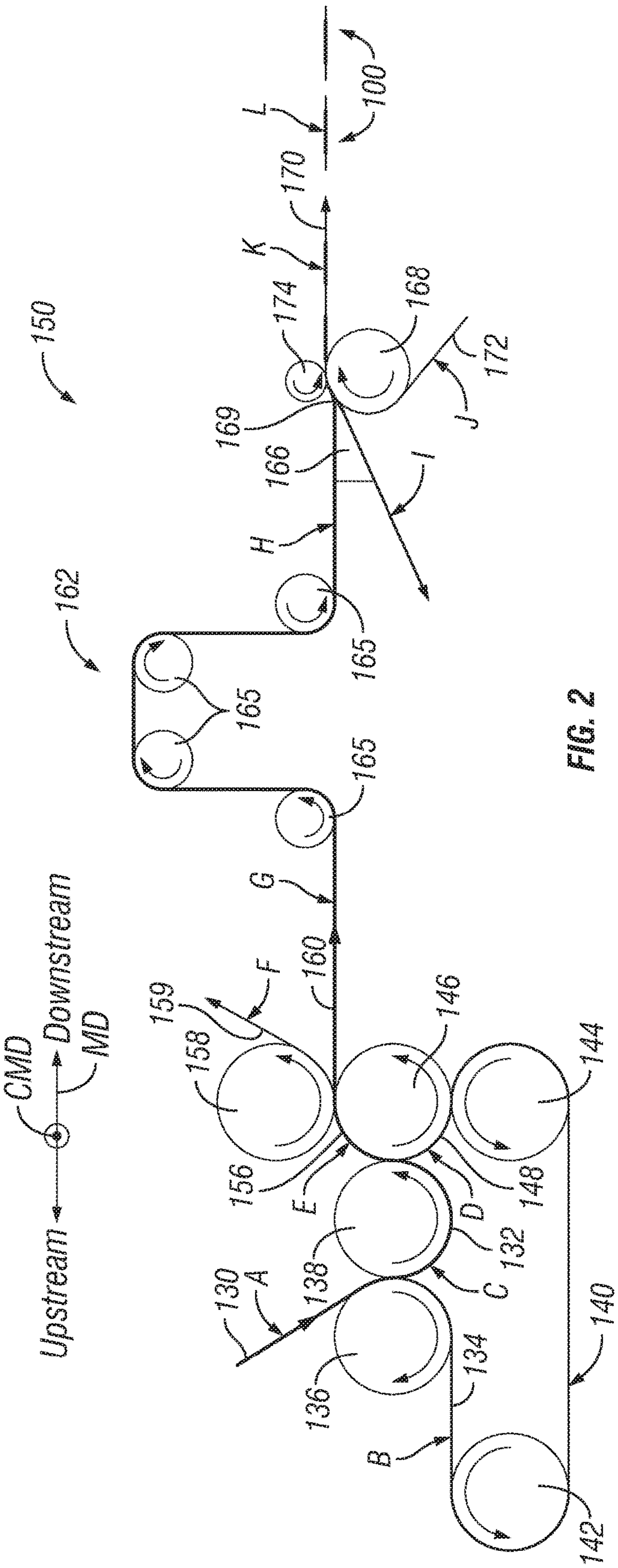
FIG. 2 is a schematic side elevational view of a web handling apparatus configured to perform methods of the present disclosure to form adhesive patch assemblies of the present disclosure.

The tab 103 can be formed from a first web used in the process illustrated in FIG. 2. Examples of first web materials are described in greater detail below. The tab 103 is at least partially adhered to the adhesive layer 112 of the patch 102, and as such, can present release characteristics to the adhesive layer 112. However, the adhesion between the patch 102 and the tab 103 can be tuned such that sufficient adhesion exists between the patch 102 and the tab 103 to facilitate using the tab 103 in transferring the patch 102 from a first web to a second web, as described in greater detail below with respect to FIG. 2, and to facilitate using the tab 103 during application of the patch 102 to a surface (e.g., to skin).

In some embodiments, the tab 103 can have a thickness of at least 0.05 mm (50 μm); in some embodiments, at least 0.08 mm (80 μm); and in some embodiments, at least 0.1 mm (100 μm). In some embodiments, the tab 103 can have a thickness of no greater than 2 mm; in some embodiments, no greater than 1 mm; in some embodiments, no greater than 0.5 mm (500 μm); in some embodiments, no greater than 0.2 mm (200 μm); and in some embodiments, no greater than 0.15 mm (150 μm).

The release liner 104 can be formed from a second web used in the process illustrated in FIG. 2. Examples of second web materials are described in greater detail below.

Generally, the tab 103 is thicker and/or more rigid than the patch 102 in a given adhesive patch assembly 100 to facilitate patch transfer during manufacturing (i.e., web handling) and patch application, as mentioned above.

The specific arrangement of the patch 102 and the tab 103 in the adhesive patch assembly 100 of FIG. 1 is shown by way of example only. As mentioned above, the leading edge 124 of the tab 103 can be positioned slightly differently with respect to the leading edge 116 of the patch 102 than what is shown in FIG. 1. In addition, the shape and size of each of the patch 102 and the tab 103, as well as the relative sizing between the patch 102 and the tab 103 (e.g., longitudinally and laterally) is shown in FIG. 1 by way of example only.

As described in greater detail below with respect to FIGS. 2 and 3H-3K, in some embodiments, the tab 103 can have a width in the CMD that is less than the width of the patch 102 in the CMD, such that at least a portion of the adhesive layer 112 is exposed in the leading portion 114 (e.g., at the leading edge 116) of the patch 102 and is not covered by the tab 103. Such a configuration can facilitate transferring the patch 102 to a downstream web, as described in greater detail below. However, this need not be the case.

Figure 4A:
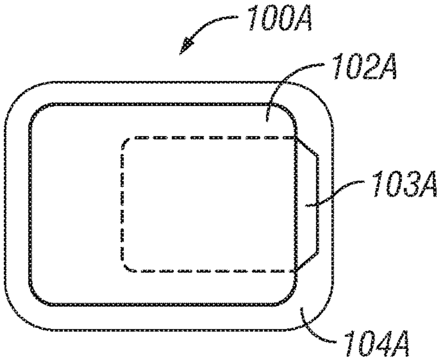
FIGS. 4A-4D are top plan views of adhesive patch assemblies according to other embodiments of the present disclosure.
Figure 4B:
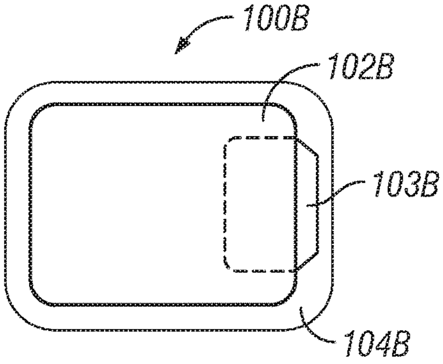
Figure 4C:
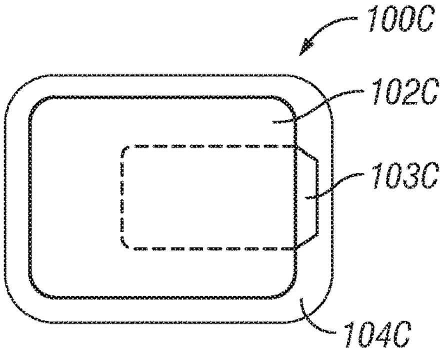
Figure 4D:
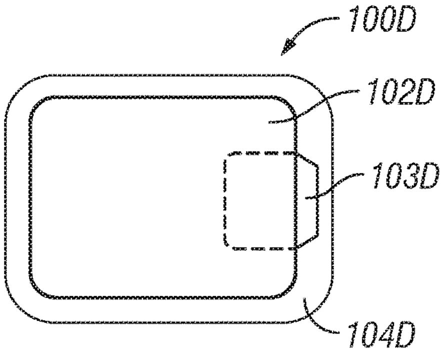

FIGS. 4A-4D illustrate adhesive patch assemblies 100A, 100B, 100C and 100D, respectively, according to other embodiments of the present disclosure. Each adhesive patch assembly 100A, 100B, 100C and 100D includes a patch 102, a tab 103 and a release liner 104 numbered in the A, B, C, and D number series, respectively. The adhesive patch assemblies 100A, 100B, 100C and 100D of FIGS. 4A-4D represent different shapes and relative sizing of the patch 102 and the tab 103. That is, even though the patch assemblies 100, 100A and 100C of FIGS. 1, 4A and 4C, respectively, each include an elongated tab 103 that overlaps more than half of the length of the patch 102 (i.e., in a machine or web direction), FIGS. 4B and 4D represent that this relative sizing need not be the case, and in some embodiments, the tab 103 can overlap less than one half of the length of the patch 102, and in some embodiments, can overlap less than ⅓ of the length of the patch 102.

However, in some embodiments, an elongated tab 103 can facilitate transfer of the patch 102 during web handling processes. In addition, an elongated tab 103 can be particularly useful in transferring relatively small patches 102 during web handling, because an elongated tab 103 can allow a small patch 102 to bridge a gap between adjacent supporting structures that may be wider than the length of the small patch 102. That is, in some embodiments, the length of the tab 103 in the machine direction can be greater than the length of the patch 102. In such embodiments, for example, the leading edge 124 of the tab 103 can extend beyond (i.e., downstream of) the leading edge 116 of the patch 102 by an amount that is equal to at least about half of the length of the tab 103.

Figure 5:
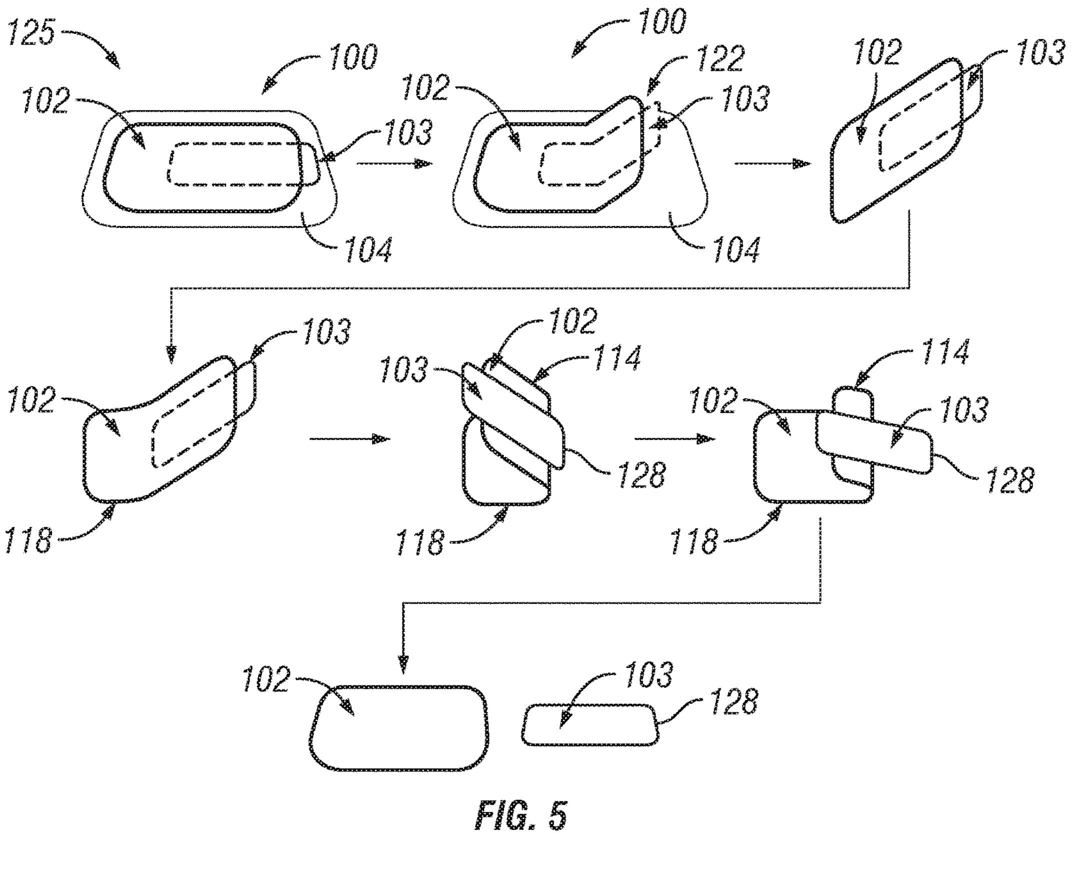
FIG. 5 illustrates a method of using the adhesive patch assembly of FIG. 1 to apply the adhesive patch, e.g., to skin, showing perspective views of the adhesive patch assembly, or portions thereof, at various stages of the method.

FIG. 5 illustrates a method 125 of applying an adhesive laminate patch according to one embodiment of the present disclosure. By way of example only, the method 125 of FIG. 5 illustrates a method of using the adhesive patch assembly 100 of FIG. 1 to apply the adhesive laminate patch 102.

In a first step of the method 125, the adhesive patch assembly 100 can be provided. At least a portion of the tab 103 (e.g., the leading portion 122 of the tab 103) can then be grasped and lifted from the release liner 104, and the tab 103 can be used to peel the patch 102 from the release liner 104 (see the second and third steps of the method 125 of FIG. 5).

As shown in a fourth step of the method 125, a portion of the patch 102 located opposite the tab 103 (e.g., the trailing portion 118 of the patch 102) can then be adhered (i.e., via the adhesive layer 112 (see FIG. 1)) to a surface of interest (e.g., a skin surface). As further shown, the entire tab 103 can then be exposed (i.e., such that the trailing edge 128 of the tab 103 is exposed) by folding the non-adhered portion of the patch 102 (e.g., comprising the leading portion 114 of the patch 102) back over the adhered portion of the patch 102 (i.e., the trailing portion 118). As shown in the last two steps of the method 125 of FIG. 5, the tab 103 can then be pushed forward in the direction of the trailing edge 128 of the tab 103 (i.e., leading with the trailing edge 128 of the tab 103) to continue laying down the patch 102 on the surface and adhering the patch 102 to the surface until the entire patch 102 is adhered to the surface and the tab 103 has been removed from the adhesive layer 112 of the patch 102.

FIG. 2 illustrates a web handling apparatus 150 according to one embodiment of the present disclosure. FIGS. 3A-3L illustrate partial plan views of one or more webs at the locations A-L, respectively, of the web handling apparatus 150 according to one method of handling adhesive laminate of the present disclosure. FIGS. 7A-7L, 8A-8L and 9A-9L show alternative web views of one or more webs at locations A-L, respectively, of the web handling apparatus 150 according to other embodiments of methods of the present disclosure.

Figure 3A:
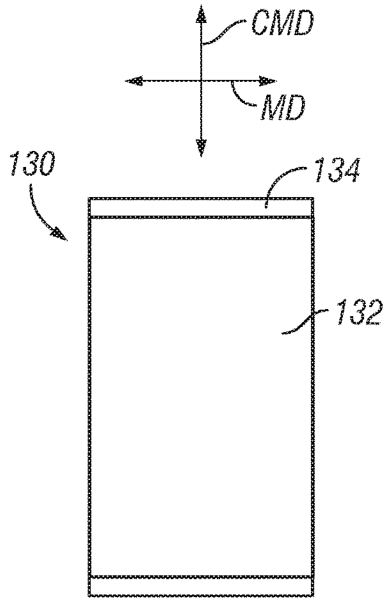
FIGS. 3A-3L are schematic partial top plan views of webs being handled by the web handling apparatus of FIG. 2, at positions A-L of FIG. 2, respectively, illustrating a method according to one embodiment of the present disclosure.
Figure 3B:
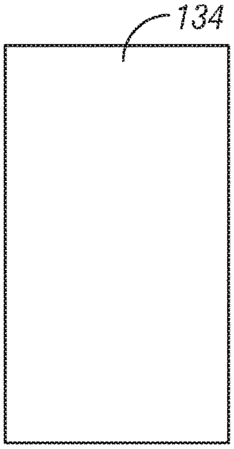
Figure 3C:
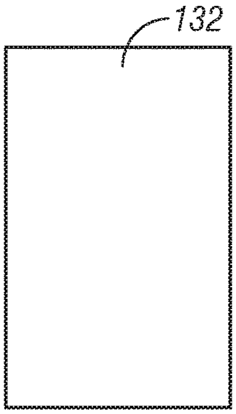

With reference to FIGS. 2 and 3A-3L, a first exemplary method of handling an adhesive laminate of the present disclosure will now be described. The web handling apparatus 150 and the webs of FIGS. 3A-3L will be described with reference to a machine, (or web) direction (MD) and a cross-machine (or cross-web, or transverse) direction (CMD), as shown in FIGS. 2 and 3A.

While only partial web views are shown in each of FIGS. 3A-3L, it should be understood that continuous webs and continuous processes can be employed, and the partial web views of FIGS. 3A-3L are snapshots in time of one or more webs at specific location (i.e., A-L) of the web handling apparatus 150. Thus, it should be understood that each of the views of FIGS. 3A-3L can continue and repeat to either side in the MD.

Position A of the apparatus 150 is located upstream in the web handling process, i.e., at an upstream portion of the apparatus 150, and position L of the apparatus 150 is located downstream in the process, i.e., at a downstream location of the apparatus 150.

In general, an event, location, or element is “upstream” of a point of reference (e.g., another event, location, or element) if it is positioned at least partially to the left of the point of reference, in the figure or on the page; and an event, location, or element is “downstream” of a point of reference (e.g., another event, location, or element) if it is positioned at least partially to the right of the point of reference, in the figure or on the page. Upstream locations, elements and processes in FIGS. 2 and 3A-3L will generally be positioned toward the left of the figure and the page, and downstream locations, elements and processes in FIGS. 2 and 3A-3L will generally be positioned toward the right of the figure and the page. In addition, a step or process of the method is “upstream” of a step of reference if it occurs at least partially prior to the step of reference, and a step or process of the method is “downstream” of a step of reference it if occurs at least partially after the step of reference.

The method 150 illustrated in FIG. 2 includes a starter web or rollstock 130 (see position A of FIGS. 2 and 3A) comprising an adhesive laminate 132 adhered to a release liner 134 being led over a first support roll 136, with the adhesive of the adhesive laminate 132 facing the first support roll 136 and the release liner 134. The rollstock 130 is then passed between a nip formed between the first support roll 136 and a second support roll 138, where the rollstock 130 is separated into its components—the adhesive laminate 132 and the release liner 134.

That is, the adhesive laminate 132 is separated from the release liner 134 as the rollstock 130 passes between the first support roll 136 and the second support roll 138, and the adhesive laminate 132 is then transferred onto the second support roll 138 in such a way that the adhesive of the adhesive laminate 132 faces away from the second support roll 138 (see position C of FIG. 2 and FIG. 3C), while the release liner 134 continues around the first support roll 136. The release liner 134 is led over the first support roll 136 in such a way that the release surface of the release liner 134 faces away from the first support roll 136. The release liner 134 is then led toward a slit/tab die cutting process 140 (see position B of FIG. 2 and FIG. 3B) comprising third support roll (e.g., an idler roll) 142 (e.g., about which the release liner 134 can be led with its release surface facing the third support roll 142), a slit/tab die (e.g., provided on a roll) 144

(e.g., about which the release liner 134 can be led with its release surface facing the die 144), and any other suitable processing structures.

Figure 3D:
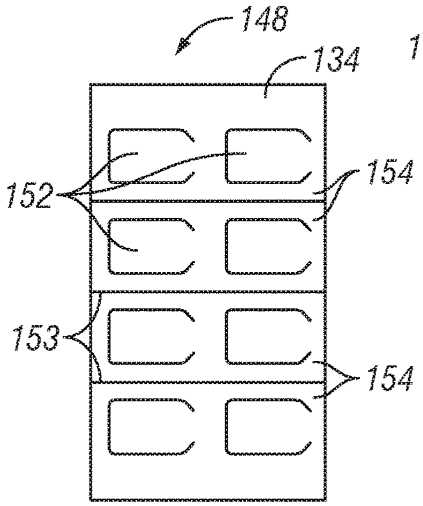

The release liner 134 can be die cut by the slit/tab die 144 as the release liner 134 is led over the die 144 and between the die 144 and a fourth support roll 146 positioned adjacent the die 144 (e.g., such that the release liner 134 can be die cut on the fourth support roll 146). In embodiments in which the fourth support roll 146 provides a surface onto which the die 144 can be pressed to cut the release liner 134, the fourth support roll 146 can be in the form of an anvil roll known to those skilled in the art. That is, the release liner 134 can be cut to form a first web 148 (see position D of FIG. 2 and FIG. 3D) comprising a plurality of partially-cut tabs 152 in the release liner 134, arranged along the MD of the first web 148, such that the partially-cut tabs 152 are spaced apart longitudinally from one another, i.e., in the MD. The tabs 152 of the embodiment of FIGS. 3A-3L are partially-cut by the die 144 and are precursors to the final tabs 103 of the end product, because, as shown in FIG. 3D, the tabs 152 are not yet completely cut from the release liner 134. Rather, the leading edge 124 of the tab 103 has not yet been cut. The partially-cut precursor tabs 152 therefore remain attached to the first web 148 at this stage in the process.

In addition, in some embodiments, as shown in FIG. 3D, the die 144 can be configured to further form at least one longitudinal (i.e., along the MD) cut 153 in the release liner 134 to form a plurality of longitudinally-extending ribbons 154, such that the partially-cut tabs 152 can also be spaced apart laterally (i.e., along the CMD). Three longitudinal cuts 153 and four ribbons 154 are shown in FIG. 3D by way of example only, but it should be understood that as few as one ribbon 154 (i.e., zero longitudinal cuts 153) and as many as structurally possible can be formed.

The term “cutting” is intended to include any suitable process that can produce tabs of the present disclosure (e.g., partially-cut tabs 152 and final tabs 103) and/or patches of the present disclosure (e.g., patches 102). Examples of suitable methods include die cutting, such as with rotary or steel-rule dies, stamping, punching, and cutting along a pattern or contour with a knife, blade, laser, or water-jet.

As shown in FIG. 2, the fourth support roll 146 is also positioned adjacent the second support roll 138. After the release liner 134 is moved through the die cutting process 140, it can be rejoined with the adhesive laminate 132. That is, after the first web 148 is formed (i.e., after the partially-cut tabs 152 are formed), the first web 148 can be led over the fourth support roll 146 in such a way that the release surface of the release liner 134 forming the first web 148 faces the second support roll 138 and faces away from the fourth support roll 146. The adhesive laminate 132 can then be transferred from the second support roll 138 onto the first web 148 on the fourth support roll 146 (e.g., as the adhesive laminate 132 and the first web 148 are led through a nip formed between the second support roll 138 and the fourth support roll 146) to form a precursor article 156 comprising the adhesive laminate 132 (i.e., the adhesive thereof) adhered to the release surface of the first web 148, such that the adhesive laminate 132 overlaps at least the portion of the first web 148 comprising the partially-cut tabs 152 (see position E of FIG. 2 and FIG. 3E).

As shown in FIG. 2, the apparatus 150 can further include a patch die 158, which can be positioned adjacent the fourth support roll 146 and can be configured to cut the adhesive laminate 132 of the precursor article 156 (e.g., on the fourth support roll 146) to form a plurality of disconnected adhesive laminate patches 102 (see FIG. 3G) and a continuous non-patch weed 159 (see FIG. 3F) adhered to the first web 148, wherein each patch 102 is aligned over and adhered to a tab 103 in the first web 148, such that a leading edge 124 of each tab 103 is located adjacent a leading edge 116 of each patch 102.

The patches 102 may be prepared, for instance, by making a controlled depth punch through the adhesive laminate 132 such that the adhesive laminate 132 is cut through its full thickness. In some embodiments, as shown in FIG. 3G, the partially-cut tabs 152 can be converted to full tabs 103 (i.e., can be completed) by the same patch die 158 used to cut the patches 102. In such embodiments, the patch die 158 can include a two-level die having a first level configured to cut the patches 102 by cutting the adhesive laminate 132 up to the first web 148, without cutting through the first web 148 (i.e., the release liner 134); and a second level configured to cut the remaining portion of the tabs 103 (e.g., the leading edge 124) by cutting through the first web 148. However, as shown in FIGS. 3G and 3H, at least a portion of each patch 102 is still adhered to an uncut portion of the first web 148 (i.e., the release liner 134), so that the patches 102 and tabs 103 are maintained in place on the web.

The patches 102 are formed (i.e., cut) while adhered to the first web 148, and can generally be cut (or punched) into the desired shape, and may be, for example, round, oval, square, rectangular, rectangular with rounded edges, or any other desired shape. In some embodiments, the patches 102 may have gaps or holes, so as to form, for example, a ring shaped patch or to form a patch having a plurality of small through-holes, such as described in United States Patent Application Publication No. 2004-0219195 (Hart et al.), the disclosure of which is herein incorporated by reference.

The non-patch weed 159 can then be separated (see position F of FIG. 2 and FIG. 3F) from the precursor article 156 (e.g., by continuing the non-patch weed 159 about the patch die 158 toward any necessary downstream handling or waste processes) to form a first article 160 comprising the plurality of disconnected adhesive laminate patches 102 adhered to the first web 148 (see position G of FIG. 2 and FIG. 3G). The non-patch weed 159 is removed, as shown at position F of FIG. 2 and FIG. 3F, and can be discarded or reused.

Figure 3E:
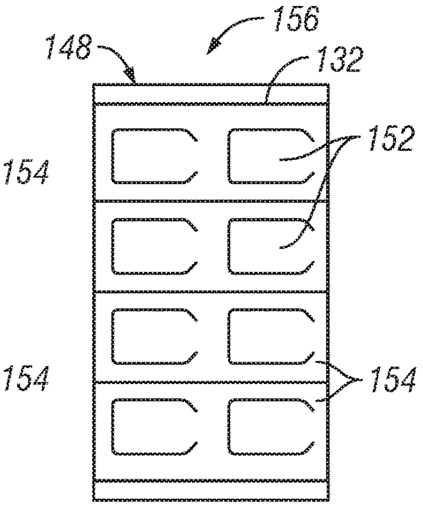
Figure 3F:
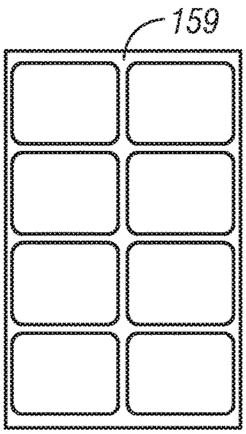
Figure 3G:
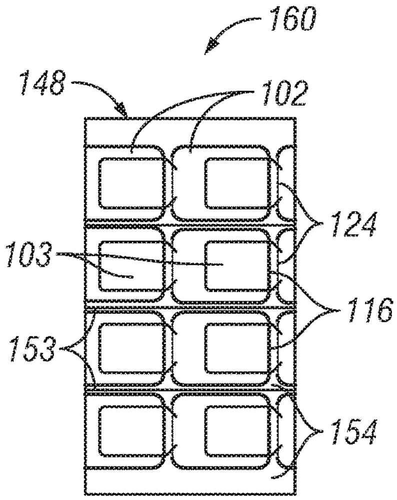
Figure 3H:
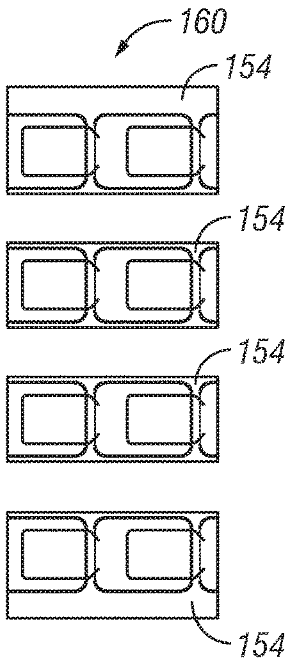

In embodiments employing a plurality of ribbons 154, the first article 160 can then be led through a ribbon guide 162 comprising a series of spreading rolls, belts or other supporting structures 165 about which the ribbons 154 can be directed in order to laterally spread and separate the ribbons 154 from one another (i.e., to spread the ribbons in the CMD), so that each ribbon 154 of the first article 160 may be further handled independently (see position H of FIG. 2 and FIG. 3H).

As shown in FIG. 2, the apparatus 150 can further include a nosebar 166 that forms a supporting structure located downstream of the patch cutting process (i.e., the patch die 158), the fourth support roll 146, and optionally, the ribbon guide 162. As further shown in FIG. 2, the apparatus 150 can further include a fifth support roll 168 positioned adjacent the nosebar 166 and separated from the nosebar 166 by a gap (or spacing) 169.

The gap 169 between the nosebar 166 and the fifth support roll 168 is defined as the closest distance between the nosebar 166 and the fifth support roll 168. The size of the gap 169 may vary, but it is generally selected so as to avoid having a long portion of unsupported patch 102 during the process of transferring the patch from the first web 148 of the first article 160 to a second web 172. The tab 103 also helps avoid this. In some embodiments, the gap 169 is selected relative to the lengthwise dimension (i.e., in the MD) of a patch 102, and, in some embodiments, can be less than 0.5 times; in some embodiments, less than 0.2 times, and in some embodiments, less than 0.1 times the lengthwise dimension of a patch 102. In some embodiments, the gap 169 may be at least 0.01 times, and in some embodiments, at least 0.05 times, the lengthwise dimension of a patch 102.

A second web 172 having a release surface (i.e., a second release liner) can be led over the fifth support roll 168 (see position J of FIG. 2 and FIG. 3J), and the second web 172 can be oriented such that the release surface of the second web 172 faces the nosebar 166 and faces away from the fifth support roll 168.

Figure 3I:
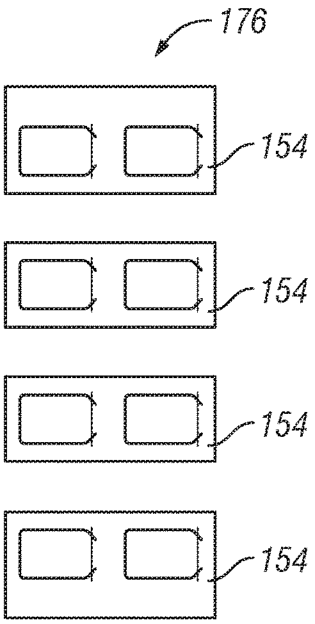
Figure 3J:
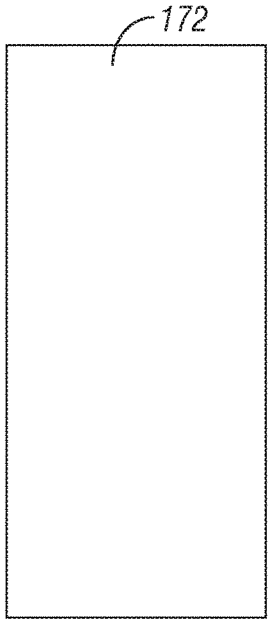
Figure 3K:
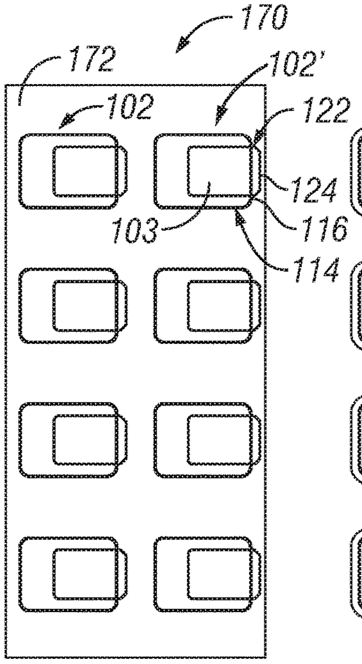
Figure 3L:
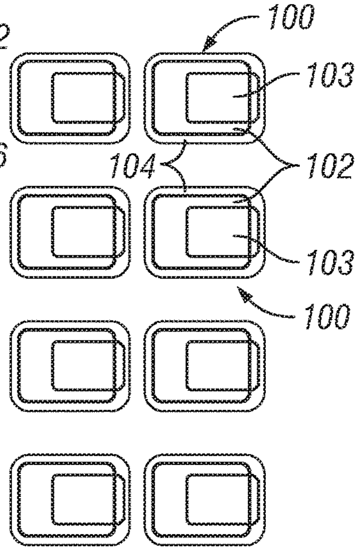

The first article 160 can be led over the nosebar 166 to cause the leading portion 122 (e.g., including the leading edge 124) of a first tab 103' and a leading portion 114 (e.g., including the leading edge 116) of a first patch 102' aligned over the first tab 103' (i.e., in each ribbon 154 if multiple ribbons 154 are employed—one is referenced in FIG. 3K for simplicity) to lift off of the first web 148 together in such a way that the leading portion 114 of the first patch 102' is supported by the first tab 103' and extends across the gap 169 between the nosebar 166 and the fifth support roll 168. That is, each tab 103 is configured to facilitate transfer of a patch 102 from the nosebar 166 to the fifth support roll 168, and particularly, to support the patch 102 as it is transferred (e.g., via an island placement process) from the first web 148 to the second web 172.

As the first patch 102' is extended from the nosebar 166 to the second web 172 on the fifth support roll 168, the leading portion 114 of the first patch 102' can be adhered to the release surface of the second web 172 on the fifth support roll 168. The second web 172 can be advanced on the fifth support roll 168 to transfer the first patch 102' from the first web 148 of the first article 160 to the second web 172 to form a second article 170 comprising a plurality of patches 102 on the second web 172, wherein the patches are spaced apart longitudinally on the second web 172 (and also laterally if multiple ribbons 154 were employed). Each patch 102 is aligned over a tab 103, such that the leading edge 124 of the corresponding tab 103 is adjacent the leading edge 116 of the patch 102 (see position K of FIG. 2 and FIG. 3K).

As mentioned above the tab 103 facilitates lifting the leading portion 114 (including the leading edge 116) of the patch 102 off of the first web 148 to allow the leading portion 114 (e.g., including the leading edge 116) of the patch 102 to be adhered onto the second web 172 and then transferred onto the second web 172. In some embodiments, it can be advantageous for the tab 103 to have a width in the CMD that is less than the width of the patch 102 in the CMD, such that the adhesive layer 112 of the patch 102 (see FIG. 1) at the leading edge 116 of the patch 102 is not covered by the tab 103 during the transfer, and the leading portion 114 of the patch 102 can be adhered to the second web 172. However, in some embodiments, the tab 103 can have the same width, or a greater width, as the patch 102 in the CMD, and the relatively greater rigidity of the tab 103 still facilitates lifting the patch 102 off of the first web 148 and transferring the patch 102 to the second web 172.

The patches 102 transferred to the second web 172 are placed in a longitudinally spaced apart fashion, otherwise referred to here as an "island placement" converting process. The second web 172 will typically serve as the final product release liner 104 and typically undergoes further converting to prepare individual patch shaped articles having a protective release liner. The longitudinal spacing between patches 102 on the second web 172 is typically achieved by running the first web 148 (i.e., the first article 160) in an intermittent motion over the nosebar 166. Alternatively, or in addition, the second web 172 can be accelerated over the fifth support roll 168 relative to the first web 148 (i.e., the first article 160) on the nosebar 166.

A non-tab weed 176 of the first web 148, which can be in the form of laterally separate ribbons 154, can be directed away from the nosebar 166 (i.e., passed completely over the nosebar 166) as the patches 102 and tabs 103 are lifted off of the first web 148 and transferred to the second web 172 (see position I of FIG. 2 and FIG. 3I). The non-tab weed 176 of the first web 148 can then be discarded or reused.

As mentioned above, advancement of the patches 102 onto the second web 172 may be obtained, for example, by momentarily stopping the motion of the first web 148 while continuing the motion of the second web 172. Since the patch 102 is placed on and adhered to the second web 172, the patch 102 and the tab 103 are thus pulled and delaminated from the first web 148 (of the first article 160, see FIG. 3H). It is not necessary, however, to stop the motion of the first web 148 (or the first article 160), as the same result may be obtained by providing a differential rate of motion between the first web 148 and the second web 172. In particular, if the first web 148 advances more slowly than the second web 172, then the patch 102 and tab 103 will be pulled away from the remainder of the first web 148. In some embodiments, the second web 172 is advanced over the fifth support roll 168 in a continuous motion (that is, without stopping) and more preferably at a substantially constant rate. In some embodiments, the first web 148 is advanced at a constant rate and the second web 172 is intermittently accelerated and decelerated in order to detach the patches 102 and longitudinally space the patches 102 on the second web 172 as desired. The second web 172 may be accelerated in a generally step-wise fashion, that is, it is rapidly accelerated to a faster speed than the first web 148 to quickly cause separation of the patch 102 and tab 103 from the remainder of the first web 148. After detachment, the second web 172 may be held at the faster speed for a given time period to obtain the desired spacing of patches 102 on the second web 172. For example, the second web 172 may be held at a uniform faster speed for a given time period and then decelerated in a step-wise fashion to substantially the same rate as the first web 148. In an alternative embodiment, the second web 172 may be gradually slowed to match the rate of the first web 148 in such a fashion as to provide the desired spacing of patches 102 on the second web 172.

Alternatively, the second web 172 may be held at a constant rate and the first web 148 can be intermittently accelerated and decelerated in order to separate the patch 102 and the tab 103 from the remainder of the first web 148.

In more general terms, the separation can be facilitated by accelerating the second web 172 relative to the first web 148. It should be understood that this relative acceleration may be accomplished by many different combinations of speeds of the first and second webs 148 and 172, including those combinations described above, but also including any other combinations of speeds. For example, both webs 148 and 172 may move in a predetermined pattern of constantly changing speeds while still providing the desired relative motion between the two webs 148 and 172.

In some embodiments, the first web 148 and the second web 172 can be moved at substantially the same speed during the time that a patch 102 and tab 103 are transferred from the first web 148 to the second web 172. The term substantially the same speed should be understood to encompass small fluctuations or differences in speed between the two webs as long as these small fluctuations or differences will not lead to any change in the process relative to the process where the speed of the two webs is identical. For example, this matching of speed is intended to minimize any stretching or tensile forces that might lead to irreversible deformation of the patch 102 while it is contact with both webs 148 and 172. Although not wishing to be bound by theory, it is believed that the patch 102 and tab 103 spanning the gap 169 is at least partially held in place by the adhesion of the portion of the patch 102 (e.g., the trailing portion 120) in contact with the first web 148 during the time that the tab 103 and the patch 102 are placed onto the second web 172.

As shown in FIG. 2, the apparatus 150 can further include one or more ironing rolls 174 positioned to press the patches 102 (and tabs 103) onto the second web 172 against the fifth support roll 168 to aid in affixing the patches 102 to the second web 172 (e.g., to minimize air bubbles between the patches 102 and the second web 172). The one or more ironing rolls 174 may be positioned such that they contact the leading portion 114 of each patch 102 before it is separated from the first web 148. This may increase the adhesive force between the patch 102 and the second web 172 prior to separation and thereby assist in separating the patch 102 from the remainder of the first web 148 (i.e., the first article 160).

In a downstream cutting process according to methods known to those of skill in the art, the second web 172 can be cut around each set of a patch 102 and tab 103 to form a plurality of adhesive patch assemblies 100 (see position L of FIG. 2 and FIG. 3L), each assembly 100 comprising a patch 102, a tab 103 and a release liner 104, as shown in FIG. 1 and described above. By way of example, the second web 172 can be cut to a size that is greater than the combination of the patch 102 and the tab 103, such that the resulting release liner 104 extends beyond the patch 102 in all directions.

The adhesive patch assemblies 100 can then be directed to a downstream packaging process, wherein the adhesive patch assembly 100 can be positioned in a package or pouch to form a finished product. Such downstream packing processes can include any packaging process suitable for the desired finished product.

Although not shown, it should be readily understood that conventional web handling means, such as wind-up rolls, tension bars, and the like, will generally be used to handle the rollstock 130 and the second web 172 before and after they are delivered to the web handling apparatus 150 shown in FIG. 2.

The first web 148 (and the release liner 134) and the second web 172 may be any conventional film having a release surface. The term release surface is used here in a broad sense as a surface from which an adhesive layer may be removed without undue deformation of the adhesive laminate. The web is intended to serve as a carrier for the adhesive laminate and will generally be a film having sufficient strength to allow handling in ordinary manufacturing processes (e.g., winding, coating, drying, etc.). Suitable webs having a release surface include conventional release liners comprising a known sheet material such as polyester, polyethylene, polypropylene, or polyethylene-coated paper. A suitable release surface may be readily determined by one skilled in the art taking into consideration the nature of the adhesive and the web material. The release surface may have a low surface energy coating (e.g., a fluoropolymer and/or silicone based coating) or it may inherently have a low surface energy. The release surface may be generally smooth or it may have surface texture, for example, to reduce the area of contact between the adhesive and the web. The web may be continuous or perforated, but is preferably continuous.

Any of the above-described support rolls 136, 138, 142, 146, 168 may be any suitable web-handling roll, including driven and idler rolls. The use of support rolls 136, 138, 142, 146, 168 as supporting structures for the webs are shown in FIG. 2 by way of example, but any other suitable supporting structure(s) may be used to support the webs, such as a fixed bar, a plurality of rollers and/or bars, belts, or combinations thereof which adequately support the webs.

In addition, the nosebar 166 is illustrated as one example of a supporting structure over which the first article 160 can be led toward the second web 172 to accomplish transfer of the patches 102 onto the second web 172. However, any other suitable supporting structure may be used in place of, or in combination with, the nosebar 166 to support the first article 160, such as a roller or combination of more than one roller and/or bar which serves to adequately support the first article 160 and allows for a desired positioning of the first article 160 with respect to the second web 172. That is, the nosebar 166 may be any suitable web-handling structure having a shape and configuration that allows the first article 160 to be brought into close proximity to the fifth support roll 168 (or other suitable supporting structure) and also allows the first web 148 to be advanced away from the fifth support roll 168 (see position I of FIG. 2) in such a fashion that patches 102 may be transferred from the first web 148 to the second web 172.

The orientation of the nosebar 166 with respect to the fifth support roll 168 may be characterized by a take-off angle. The take-off angle is the angle between the direction of motion of the first web 148 in the first article 160 at the point where a patch 102 is transferred and the direction of advancement of the second web 172 as it moves away from the nosebar 166. For example, a tangent line can be drawn at the point on the fifth support roll 168 where the patch 102 is transferred to the second web 172. A suitable take-off angle may vary depending on a number of factors including, for example, the types of materials and thicknesses of the adhesive laminate 132, the first web 148, and the second web 172, and the shapes and sizes of the patches 102, the fifth support roll 168, and the nosebar 166. The take-off angle is generally between 0 and 180 degrees, often between 50 and 160 degrees, and sometimes between 100 and 140 degrees.

The entire process and web handling apparatus 150 illustrated in FIG. 2 is shown by way of example only. However, some embodiments of methods of the present disclosure can include only a portion of the process (e.g., using only a portion of the apparatus 150) illustrated in FIG. 2. For example, the adhesive laminate 132 and the release liner 134 are shown in FIG. 2 as coming from the same rollstock 130 and being separated, such that the release liner 134 can be directed temporarily away from the adhesive laminate 132 to be cut to form the first web 148 comprising the tabs 152, and then the adhesive laminate can be re-adhered to the same release liner 134 (i.e., the first web 148) to form the precursor article 156. However, this need not be the case. In some embodiments, the adhesive laminate 132 can come from a first source (e.g., provided in rolled form), and the release liner 134 can from a second source (e.g., provided in rolled form), without ever having been joined together in the form of the rollstock 130.

Alternatively, the first web 148 can be provided already cut to include tabs 152 from a second source, and the method may not itself actually include the process of cutting the tabs 152 to form the first web 148. As a result, some methods of the present disclosure can begin at position D of FIG. 2, where the adhesive laminate 132 is provided on a first supporting structure (e.g., the second support roll 138 of FIG. 2), and the first web 148 (already comprising the tabs 152) can be provided on a second supporting structure (e.g., the fourth support roll 146 of FIG. 2).

In other embodiments, the method can begin after the adhesive laminate 132 has been adhered to the first web 148 over the tabs 152, such that the method begins at position E of FIG. 2 with providing the precursor article 156.

Still, in other embodiments, the method can being after the patches 102 have been cut into the adhesive laminate 132 on the precursor article 156 (and optionally also after the partially-cub tabs 152 have been completely cut to form the tabs 103) and after the non-patch weed 159 has been removed from the precursor article 156, such that the method begins at position G of FIG. 2 with providing the first article 160.

As mentioned above, the multiple longitudinal ribbons 154 are optional, such that the method also may not include any spreading of ribbons 154, or the method can begin with providing already separated ribbons 154 of the first article 160. In such cases, the method can begin at position H of FIG. 2 with providing the first article 160 (either singly or in ribbons 154).

Thus, in some embodiments, the method can begin at about position H of FIG. 2, and the nosebar 166 can be referred to as a first supporting structure, and the fifth support roll 168 can be referred to as a second supporting structure. In addition, the method need not include all of the finishing steps, such as cutting the second web 172 into individual release liners 104, etc. In such embodiments, various upstream steps and processes can be used to produce the starting first article 160, and the full process described with respect to FIGS. 2 and 3A-3L is shown by way of example. Thus, in such embodiments, the particular upstream steps and elements of FIGS. 2 and 3A-3L can include providing a third supporting structure (e.g., the second support roll 138) and a fourth supporting structure (e.g., the fourth support roll 146).

FIGS. 7A-7L, 8A-8L and 9A-9L illustrate other alternative methods of the present disclosure, again with reference to FIG. 2. Even in the methods of FIGS. 7A-7L, 8A-8L and 9A-9L, the entire process that is shown is shown by way of example, and those processes can also instead begin at any of the above-described alternative starting positions.

Figure 6A:
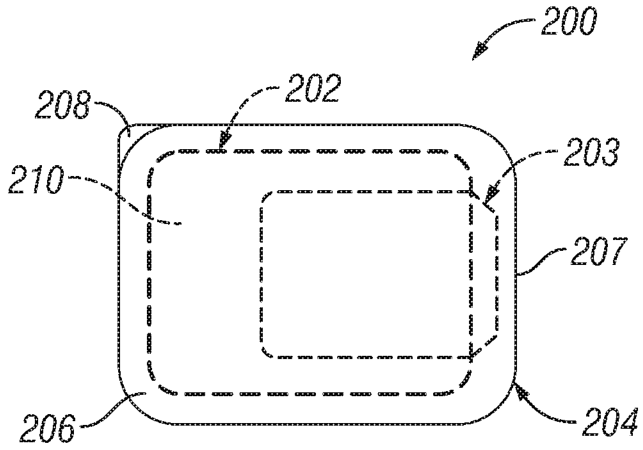
FIG. 6A is a top plan view of an adhesive patch assembly according to another embodiment of the present disclosure, the adhesive patch assembly shown assembled (i.e., in a folded configuration).
Figure 6B:
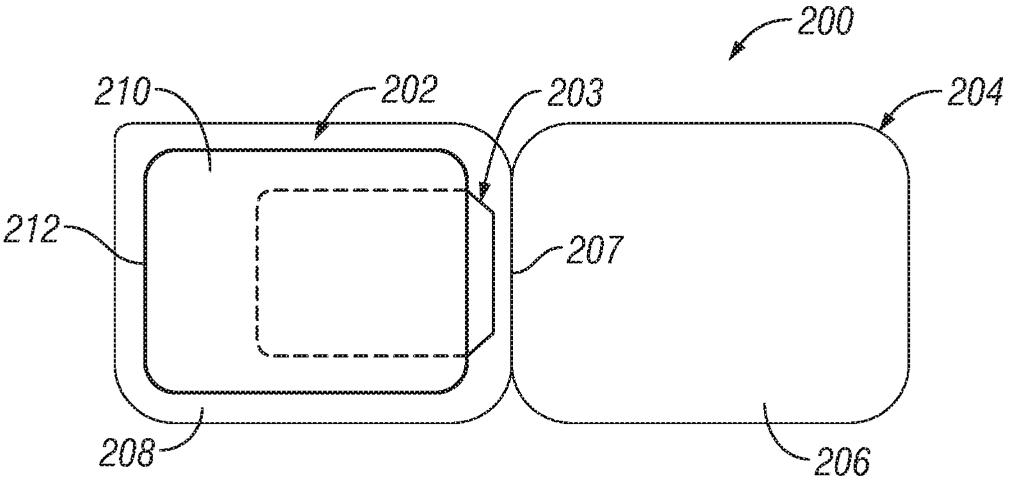
FIG. 6B is a top plan view of the adhesive patch assembly of FIG. 6A, shown unassembled (i.e., in an unfolded configuration).

FIGS. 6A and 6B illustrate an adhesive patch assembly 200 according to another embodiment of the present disclosure, wherein like numerals represent like elements. FIG. 6A shows the adhesive patch assembly 200 assembled (i.e., in a folded configuration), and FIG. 6B shows the adhesive patch assembly 200 unassembled (i.e., in an unfolded configuration). The adhesive patch assembly 200 shares many of the same elements, features, and functions as the adhesive patch assembly 100 described above with respect to FIGS. 1-3L and 5. Reference is made to the description above accompanying FIGS. 1-3L and 5 for a more complete description of the features and elements (and alternatives to such features and elements) of the embodiments illustrated in FIGS. 6A-6B. Any of the features described above with respect to FIGS. 1-3L and 5 can be applied to the embodiments of FIGS. 6A-6B, and vice versa.

The adhesive patch assembly 200 includes an adhesive laminate patch 202, a tab 203, and a release liner 204. The release liner 204 can include a first portion 206 and a second portion 208 that are at least partially coupled to one another and separated by at least one of a fold and/or hinge 207, such that the first portion 206 and the second portion 208 can be folded over one another into an overlapping relationship. In some embodiments, the fold and/or hinge 207 can be at least partially formed by one or more uncut points that serve as an anchor point to allow the first portion 206 and the second portion 208 to remain coupled together during manufacturing.

As shown, the first portion 206 can be folded over a backing 210 of the patch 202, and an adhesive layer 212 (see FIG. 6B) can be adhered to a release surface of the second portion 208 of the release liner 204. As such, the second portion 208 can function as the "primary liner," and the first portion 206 can function as the "cover liner" or the "overlay liner." The first portion (or overlay liner) 206 can remain coupled to the second portion (or primary liner) 208 during manufacturing, packaging and storage, and can be removed from the second portion 208 when the patch 202 is to be used. The first portion 206 of the release liner 204 remains at least partially coupled to the second portion 208 of the release liner 204 during packaging and storage, such that should any cold flow or migration of the adhesive layer 212 occur (e.g., during packaging and/or storage), the first portion (or cover liner) 206 of the release liner 204 will remain in position over the patch 202 and the second portion 208 of the release liner 204 to inhibit the adhesive layer 212 from adhering to any pouch or packaging material, which may inhibit removal of the patch 202 from its package and/or proper application of the patch 202.

Methods of the present disclosure can be modified to form adhesive patch assemblies comprising the release liner 204 (i.e., which include an overlay liner) by controlling the relative motion (e.g., speeds) of the first article 160 (including the first web 148) and the second web 172 in order to space the patches out appropriately (i.e., longitudinally) on the second web to allow space for the first portion (or overlay liner) 206 to be cut from the second web, in addition to the second portion 208. Then, when the second web is cut to form individual release liners around each patch, the release liner shape comprising an overlay liner, such as that shown in FIGS. 6A and 6B can be formed.

Additional details regarding release liners that can include an overlay liner and systems and methods of making same can be found in U.S. Patent Application Publication No. 2014/0303574 (Knutson), which is incorporated herein by reference in its entirety.

Additional exemplary embodiments of methods and adhesive patch assemblies of the present disclosure will now be described with respect to FIGS. 7A-7L, 8A-8L and 9A-9L. FIGS. 7A-7L, 8A-8L and 9A-9L illustrate various methods and adhesive patch assemblies of the present disclosure, wherein like numerals represent like elements. The methods and adhesive patch assemblies of FIGS. 7A-7L, 8A-8L and 9A-9L share many of the same elements, features, and functions as the methods and adhesive patch assembly 100 described above with respect to FIGS. 1-3L and 5. Reference is made to the description above accompanying FIGS. 1-3L and 5 for a more complete description of the features and elements (and alternatives to such features and elements) of the embodiments illustrated in FIGS. 7A-7L, 8A-8L and 9A-9L. Any of the features described above with respect to FIGS. 1-3L and 5 can be applied to the embodiments of FIGS. 7A-7L, 8A-8L and 9A-9L, and vice versa.

FIGS. 7A-7L illustrate partial plan views of one or more webs at the locations A-L, respectively, of the web handling apparatus 150 of FIG. 2 according to one method of handling adhesive laminate of the present disclosure.

With reference to FIGS. 2 and 7A-7L, another exemplary method of handling an adhesive laminate of the present disclosure will now be described. The web handling apparatus 150 and the webs of FIGS. 7A-7L will be described with reference to a machine, (or web) direction (MD) and a cross-machine (or cross-web, or transverse) direction (CMD), as shown in FIGS. 2 and 7A.

Figure 7A:
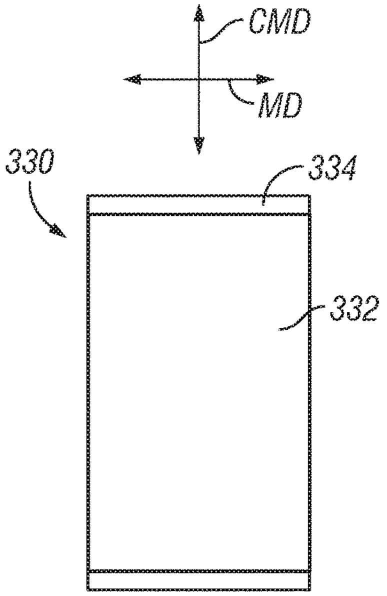
FIGS. 7A-7L are schematic partial top plan views of webs being handled by the web handling apparatus of FIG. 2, at positions A-L of FIG. 2, respectively, illustrating a method according to another embodiment of the present disclosure.
Figure 7B:
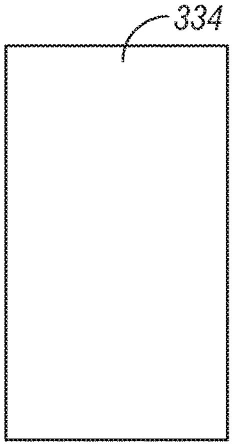
Figure 7C:
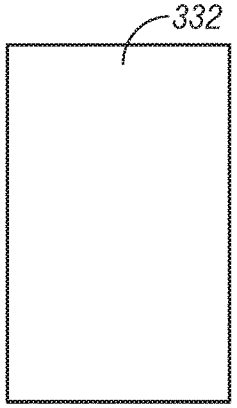

The method illustrated in FIGS. 7A-7L is similar to that of FIGS. 3A-3L, and will be described with reference numerals in the 300 series. As shown, FIGS. 7A-7C are the same as FIGS. 3A-3C and include providing a rollstock 330 comprising an adhesive laminate 332 on a release liner 334 (see position A of FIG. 2 and FIG. 7A) and then separating the adhesive laminate 332 from the release liner 334 (see positions B and C of FIG. 2 and FIGS. 7B and 7C). The release liner 334 is cut, as described above, to form a first web 348 comprising partially cut tabs 352 that are spaced longitudinally from one another (see position D of FIG. 2 and FIG. 7D). However, unlike in FIG. 3D, a leading edge 324 of each tab 352 is cut, and the partially-cut tabs 352 remain partially-cut and attached to the release liner 334 (of the first web 348) by one or more tie points (or uncut points) 355. By way of example only, each tab 352 is illustrated as including two tie points 355 located on either lateral side of the tab 352 and positioned more toward the leading edge 324 than a trailing edge 328.

Figure 7D:
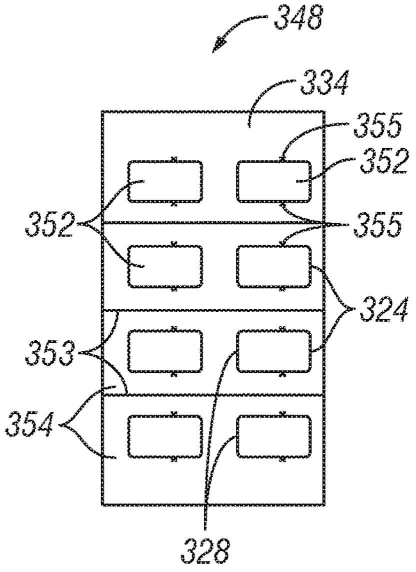
Figure 7E:
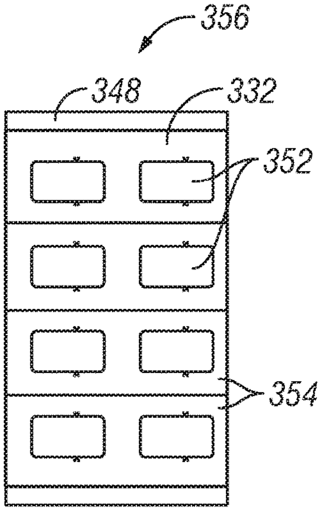
Figure 7F:
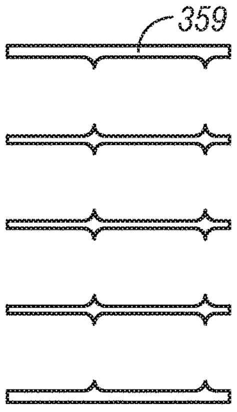

The steps of the method shown by FIGS. 7E and 7F are the same as those of FIGS. 3E and 3F in that the adhesive laminate 332 is adhered to the first web 348 comprising the partially-cut tabs 352 to form a precursor article 356 (see position E of FIG. 2 and FIG. 7E). Then, the patches 302 are cut in the adhesive laminate 332, and the non-patch weed 359 is removed (see position F of FIG. 2 and FIG. 7F), to form a first article 360 comprising the patches 302 adhered over the tabs 352 on the first web 348 (see FIG. 7G).

Figure 7G:
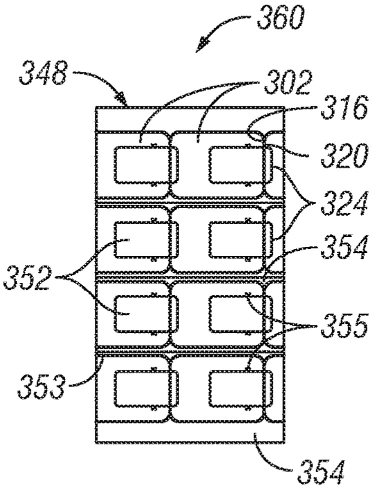
Figure 7H:
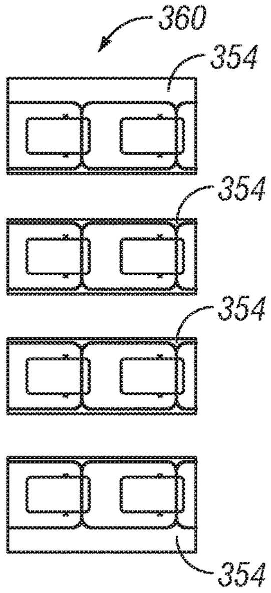
Figure 7I:
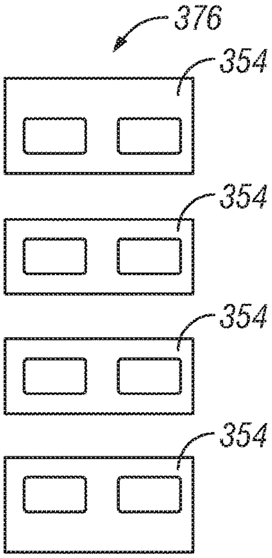
Figure 7J:
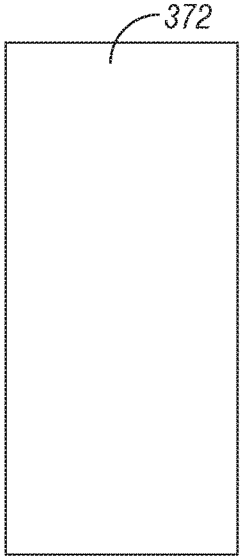

As shown in FIG. 7G, a leading edge 316 of each patch 302 is still aligned to be adjacent a leading edge 324 of each partially-cut tab 352. However, unlike the first article 160 of FIG. 3G, the tabs 352 are still only partially-cut and still include the tie points 355. In addition, because the leading edge 324 of the tabs 352 was already cut, the patch die 158 (see FIG. 2) can include only a one-level die for cutting just the patches 302 from the adhesive laminate 332, because the partially-cut tabs 352 were not cut further by the patch die 158. In addition, as shown in FIG. 7G, the patches 302 are not spaced longitudinally from one another in the first article 360, but rather the patches 302 of the first article 360 abut longitudinally, such that a trailing edge 320 of a first patch 302 directly abuts, and is formed by the same cut as, a leading edge 316 of a second patch 302. Such a cutting process and patch/tab configuration can eliminate even more waste.

Figure 7K:
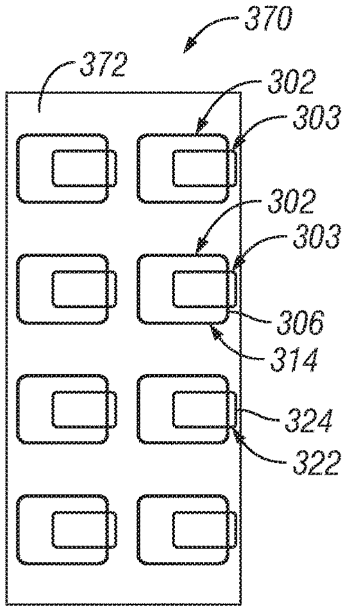
Figure 7L:
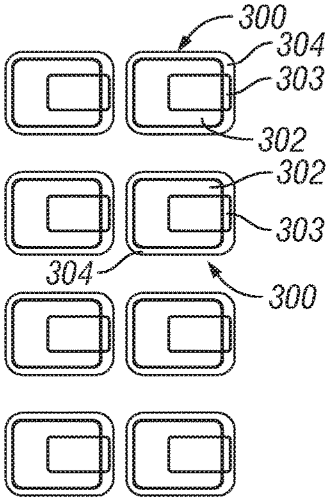

The slit/tab die 144 (see FIG. 2) can form one or more substantially longitudinal cuts 353 such that the first web 348 of FIG. 7D includes two or more ribbons 354. As such, the ribbon guide 162 (see FIG. 2) can be used to laterally separate (i.e., spread) the ribbons 354 of the first article 360 (see position H of FIG. 2 and FIG. 7H). The process represented by positions I-L of FIG. 2 can then be substantially the same as that described above with respect to FIGS. 3I-L. Namely, a second web 372 (see position J of FIG. 2 and FIG. 7J) can be provided, and the patches 302 and tabs 303 can be transferred from the first web 348 of the first article 360 onto the second web 372 to form a second article 370 (see position K of FIG. 2 and FIG. 7K), and the non-tab weed 376 of each ribbon 354 from the first web 348 of the first article 360 can be removed (see position I of FIG. 2 and FIG. 7I). As shown in FIG. 7K, the second article 370 includes the patches 302 and the tabs 303 longitudinally spaced (and optionally, also laterally spaced if multiple ribbons 354 were employed) on the second web 372. As shown at position L of FIG. 2 and FIG. 7L, the second web 372 can then be cut around each set of patch 302 and tab 303 to form adhesive patch assemblies 300 of the present disclosure, including individual release liners 304.

The same relative motion between the second web 372 and the first web 348 (i.e., the first article 360) as described above can be used in the method of FIGS. 7A-7L, such that the relatively higher speed (i.e., no matter how it is achieved) of the second web 372 relative to the first web 348 causes a leading portion 314 (including the leading edge 316) of each patch 302 and a leading portion 322 (including the leading edge 324) of each partially-cut tab 352 to be pulled by the second web 372 and thereby exert a force sufficient to cause the tie points 355 of each tab 352 to be fractured, causing a completely formed tab 303 and patch 302 to be pulled from the first web 348 of the first article 360 to form the second article 370.

FIGS. 8A-8L illustrate partial plan views of one or more webs at the locations A-L, respectively, of the web handling apparatus 150 of FIG. 2 according to one method of handling adhesive laminate of the present disclosure.

With reference to FIGS. 2 and 8A-8L, another exemplary method of handling an adhesive laminate of the present disclosure will now be described. The web handling apparatus 150 and the webs of FIGS. 8A-8L will be described with reference to a machine, (or web) direction (MD) and a cross-machine (or cross-web, or transverse) direction (CMD), as shown in FIGS. 2 and 8A.

The method illustrated in FIGS. 8A-8L is substantially similar to that of FIGS. 7A-7L, and will be described with reference numerals in the 400 series. The main difference between the method of FIGS. 8A-8L and that of FIGS. 7A-7L is that in FIGS. 8A-8L, the release liner 434 is cut to allow the patches 402 to abut not only in the MD direction but also in the CMD, thereby further minimizing waste.

Figure 8A:
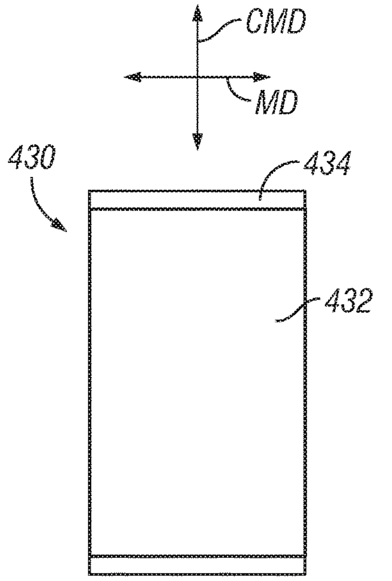
FIGS. 8A-8L are schematic partial top plan views of webs being handled by the web handling apparatus of FIG. 2, at positions A-L of FIG. 2, respectively, illustrating a method according to another embodiment of the present disclosure.
Figure 8B:
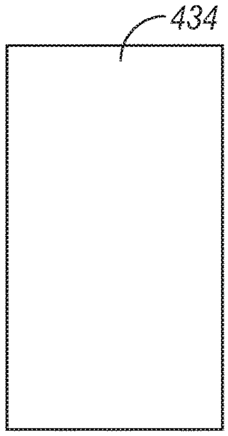
Figure 8C:
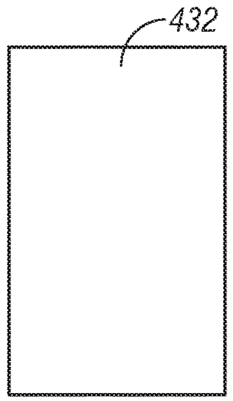
Figure 8D:
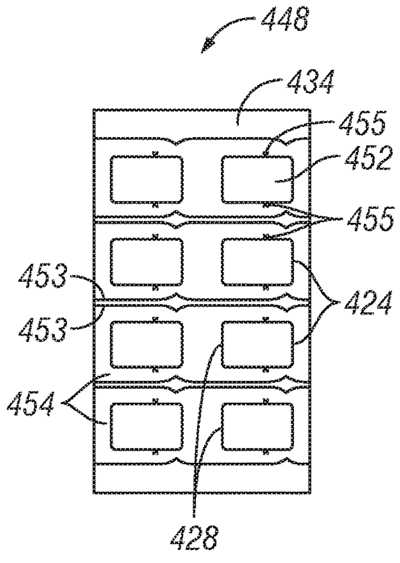

As shown, FIGS. 8A-8C are the same as FIGS. 3A-3C and FIGS. 7A-7C and include providing a rollstock 430 comprising an adhesive laminate 432 on a release liner 434 (see position A of FIG. 2 and FIG. 8A) and then separating the adhesive laminate 432 from the release liner 434 (see positions B and C of FIG. 2 and FIGS. 8B and 8C). The release liner 434 is cut, as described above, to form a first web 448 comprising partially cut tabs 452 that are spaced longitudinally from one another (see position D of FIG. 2 and FIG. 8D). As shown in FIG. 8D, a leading edge 424 of each tab 452 is cut, and the partially-cut tabs 452 remain partially-cut and attached to the release liner 434 (of the first web 448) by one or more tie points (or uncut points) 455. By way of example only, each tab 452 is illustrated as including two tie points 455 located on either lateral side of the tab 452 and positioned more toward the leading edge 424 than a trailing edge 428.

As further shown in FIG. 8D, the slit/tab die 144 (see FIG. 2) can also form one or more longitudinal cuts 453 such that the first web 448 of FIG. 8D includes two or more ribbons 454. However, in the first web 448 of FIG. 8D, each ribbon 454 is formed by two substantially longitudinal cuts 453 that are shaped and positioned, such that when patches 402 are later cut on the first web 448, the patches 402 can abut one another not only longitudinally (i.e., in the MD), but also laterally (i.e., in the CMD).

Figure 8E:
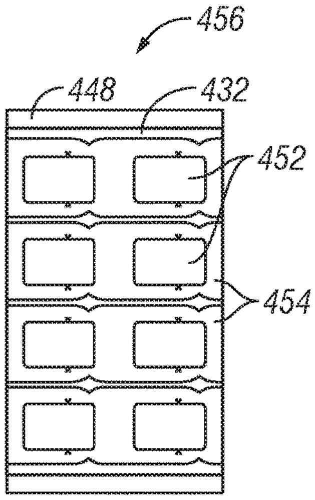
Figure 8F:
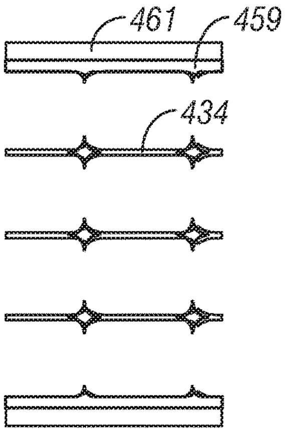

The steps of the method shown by FIGS. 8E and 8F are the same as those of FIGS. 3E-3F and 7E-7F described above in that the adhesive laminate 432 is adhered to the first web 448 comprising the partially-cut tabs 452 to form a precursor article 456 (see position E of FIG. 2 and FIG. 8E). Then, the patches 402 are cut in the adhesive laminate 432, and the non-patch weed 459, along with a non-ribbon weed 461 from the first web 448, are removed (see position F of FIG. 2 and FIG. 8F), to form a first article 460 comprising the patches 402 adhered over the tabs 452 on the first web 448 (see FIG. 8G). The non-ribbon weed 461 can include strips of release liner 434 that are pulled up from under the lateral edges of the patches 402, such that removal of the liner weed (i.e., the non-ribbon weed 461) can require slight flexing of edges of the patches 402, as described in U.S. Pat. No. 8,608,889 (Sever, et. al.), which is incorporated herein by reference in its entirety.

Figure 8G:
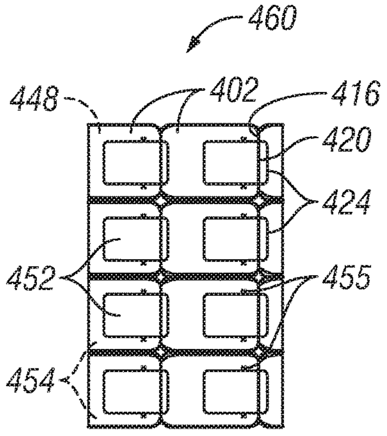

As shown in FIG. 8G, a leading edge 416 of each patch 402 is still aligned to be adjacent a leading edge 424 of each partially-cut tab 452. However, unlike the first article 160 of FIG. 3G, the tabs 452 are still only partially-cut and still include the tie points 455. In addition, because the leading edge 424 of the tabs 452 was already cut, the patch die 158 (see FIG. 2) can include only a one-level die for cutting just the patches 402 from the adhesive laminate 432, because the partially-cut tabs 452 were not cut further by the patch die 158. In addition, as shown in FIG. 8G, the patches 402 are not spaced longitudinally from one another in the first article 460, but rather the patches 402 of the first article 460 abut longitudinally, such that a trailing edge 420 of a first patch 402 directly abuts, and is formed by the same cut as, a leading edge 416 of a second patch 402. As further shown in FIG. 8G, the patches 402 also abut laterally (i.e., in the CMD). Such a cutting process and patch/tab configuration can eliminate even more waste.

Figure 8H:
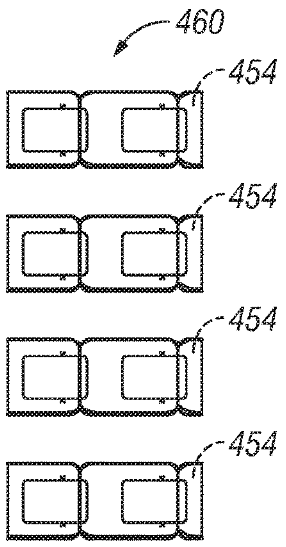
Figure 8I:
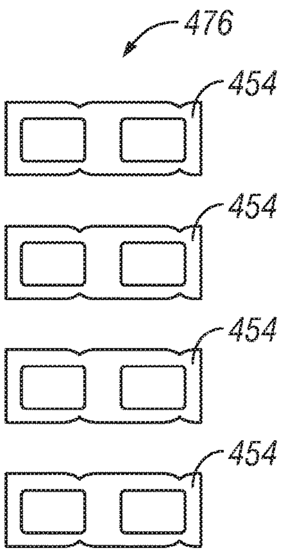
Figure 8J:
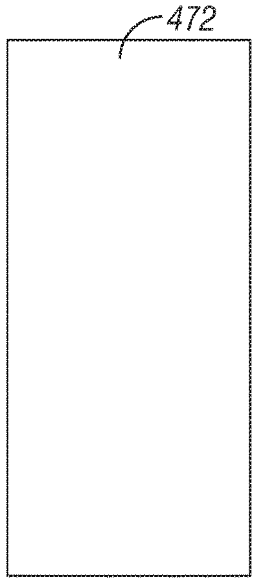
Figure 8K:
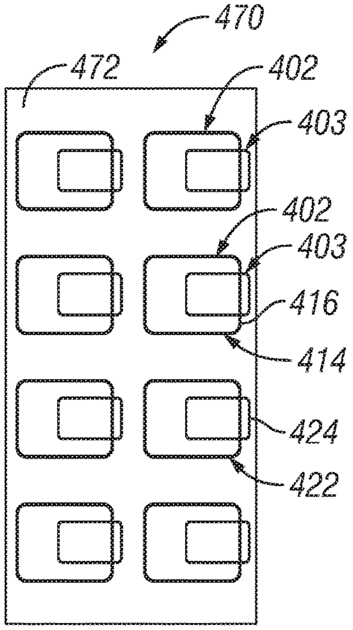
Figure 8L:
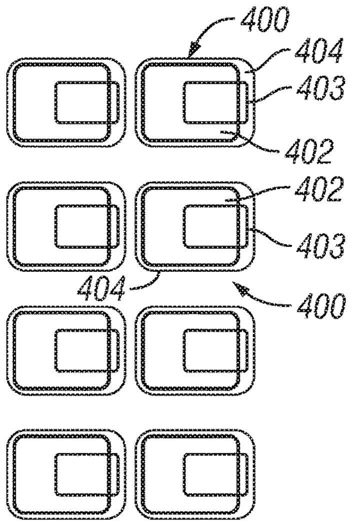

The ribbon guide 162 (see FIG. 2) can then be used to laterally separate (i.e., spread) the ribbons 454 of the first article 460 (see position H of FIG. 2 and FIG. 8H). The process represented by positions I-L of FIG. 2 can then be substantially the same as that described above with respect to FIGS. 3I-L. Namely, a second web 472 (see position J of FIG. 2 and FIG. 8J) can be provided, and the patches 402 and tabs 403 can be transferred from the first web 448 of the first article 460 onto the second web 472 to form a second article 470 (see position K of FIG. 2 and FIG. 8K), and the non-tab weed 476 of each ribbon 454 from the first web 448 of the first article 460 can be removed (see position I of FIG. 2 and FIG. 8I). As shown in FIG. 8K, the second article 470 includes the patches 402 and the tabs 403 longitudinally spaced (and optionally, also laterally spaced if multiple ribbons 454 were employed) on the second web 472. As shown at position L of FIG. 2 and FIG. 8L, the second web 472 can then be cut around each set of patch 402 and tab 403 to form adhesive patch assemblies 400 of the present disclosure, including individual release liners 404.

The same relative motion between the second web 472 and the first web 448 (i.e., the first article 460) as described above can be used in the method of FIGS. 8A-8L, such that the relatively higher speed (i.e., no matter how it is achieved) of the second web 472 relative to the first web 448 causes a leading portion 414 (including the leading edge 416) of each patch 402 and a leading portion 422 (including the leading edge 424) of each partially-cut tab 452 to be pulled by the second web 472 and thereby exert a force sufficient to cause the tie points 455 of each tab 452 to be fractured, causing a completely formed tab 403 and patch 402 to be pulled from the first web 448 of the first article 460 to form the second article 470.

FIGS. 9A-9L illustrate partial plan views of one or more webs at the locations A-L, respectively, of the web handling apparatus 150 of FIG. 2 according to one method of handling adhesive laminate of the present disclosure. The method illustrated in FIGS. 9A-9L is substantially similar to that of FIGS. 3A-3L and 8A-8L, and will be described with reference numerals in the 500 series. Particularly, FIGS. 9A-9L illustrate a method that includes a combination of the methods of FIGS. 3A-3L and FIGS. 8A-8L, because the first web 548 includes partially-cut tabs 552 that are partially cut because they are missing a leading edge 524 (similar to the first web 148 of FIG. 3D), but also includes ribbons 554 that are each formed by two substantially longitudinal cuts 553 to allow patches 502 to be formed that abut longitudinally (i.e., in the MD) and laterally (i.e., in the CMD).

With reference to FIGS. 2 and 9A-9L, another exemplary method of handling an adhesive laminate of the present disclosure will now be described. The web handling apparatus 150 and the webs of FIGS. 9A-9L will be described with reference to a machine, (or web) direction (MD) and a cross-machine (or cross-web, or transverse) direction (CMD), as shown in FIGS. 2 and 9A.

Figure 9A:
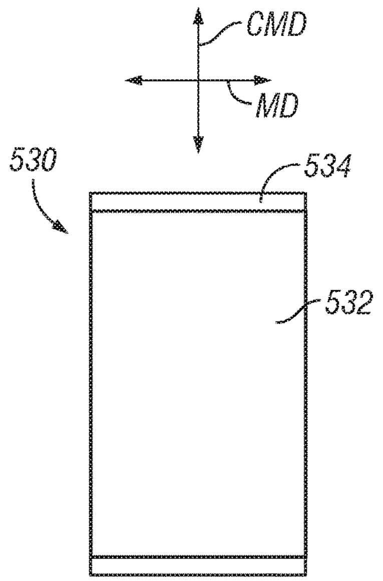
FIGS. 9A-9L are schematic partial top plan views of webs being handled by the web handling apparatus of FIG. 2, at positions A-L of FIG. 2, respectively, illustrating a method according to another embodiment of the present disclosure.
Figure 9B:
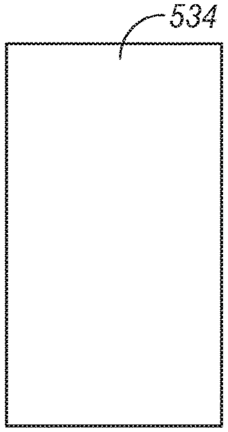
Figure 9C:
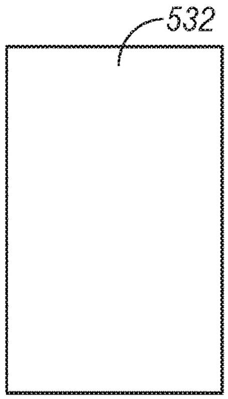
Figure 9D:
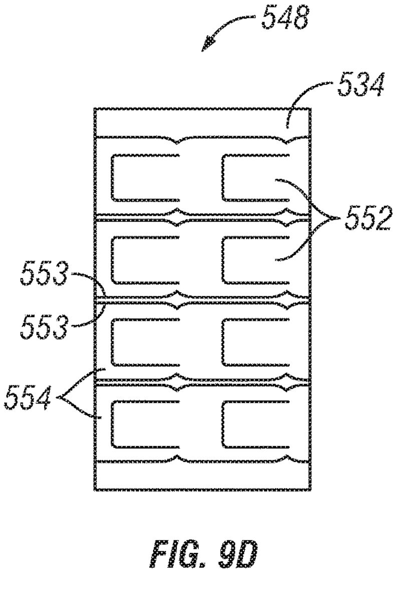

As shown, FIGS. 9A-9C are the same as FIGS. 3A-3C and FIGS. 7A-7C and include providing a rollstock 530 comprising an adhesive laminate 532 on a release liner 534 (see position A of FIG. 2 and FIG. 9A) and then separating the adhesive laminate 532 from the release liner 534 (see positions B and C of FIG. 2 and FIGS. 9B and 9C). The release liner 534 is cut, as described above, to form a first web 548 comprising partially cut tabs 552 that are spaced longitudinally from one another (see position D of FIG. 2 and FIG. 9D). As shown in FIG. 9D, the tabs 552 are partially-cut and are precursors to the final tabs 503 of the end product, because, as shown in FIG. 9D, the tabs 552 are not yet completely cut from the release liner 534. Rather, a leading edge of the tab has not yet been cut. The partially-cut precursor tabs 552 therefore remain attached to the first web 548 at this stage in the process.

As further shown in FIG. 9D, the slit/tab die 144 (see FIG. 2) can also form one or more longitudinal cuts 553 such that the first web 548 of FIG. 9D includes two or more ribbons 554. Similar to the first web 448 of FIG. 8D, each ribbon 554 of FIG. 9D is formed by two substantially longitudinal cuts 553 that are shaped and positioned, such that when patches 502 are later cut on the first web 548, the patches 502 can abut one another not only longitudinally (i.e., in the MD), but also laterally (i.e., in the CMD).

Figure 9E:
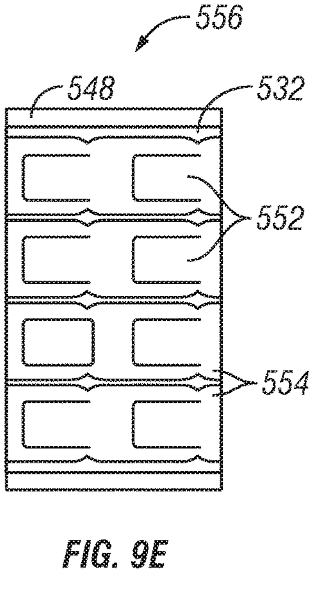
Figure 9F:
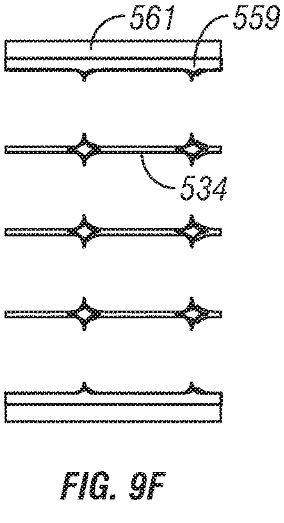

The steps of the method shown by FIGS. 9E and 9F are the same as those of FIGS. 3E-3F described above in that the adhesive laminate 532 is adhered to the first web 548 comprising the partially-cut tabs 552 to form a precursor article 556 (see position E of FIG. 2 and FIG. 9E). Then, the patches 502 are cut in the adhesive laminate 532, and the non-patch weed 559, along with a non-ribbon weed 561 from the first web 548, are removed (see position F of FIG. 2 and FIG. 9F), to form a first article 560 comprising the patches 502 adhered over the tabs 503 on the first web 548 (see FIG. 9G). The non-ribbon weed 561 can include strips of release liner 534 that are pulled up from under the lateral edges of the patches 502, such that removal of the liner weed (i.e., the non-ribbon weed 561) can require slight flexing of edges of the patches 502.

Figure 9G:
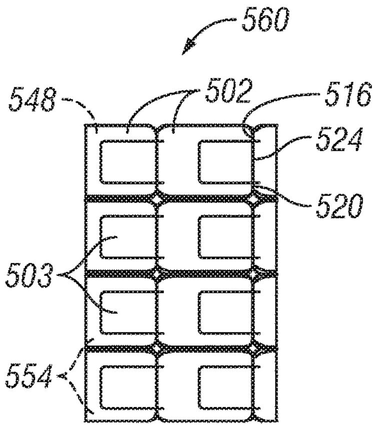

As further shown in FIG. 9G, a leading edge 516 of each patch 502 is still aligned to be adjacent a leading edge 524 of each tab 503. In addition, as shown in FIG. 9G, the patches 502 are not spaced longitudinally from one another in the first article 560, but rather the patches 502 of the first article 560 abut longitudinally, such that a trailing edge 520 of a first patch 502 directly abuts, and is formed by the same cut as, a leading edge 516 of a second patch 502. As further shown in FIG. 9G, the patches 502 also abut laterally (i.e., in the CMD). Such a cutting process and patch/tab configuration can eliminate even more waste.

Figure 9H:
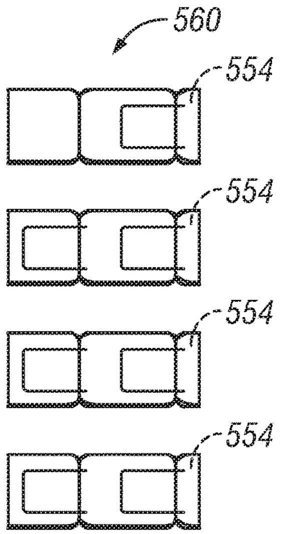
Figure 9I:
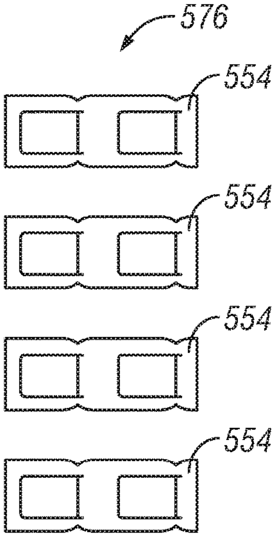

As further shown in FIG. 9G, in some embodiments, the partially-cut tabs 552 can be converted to full tabs 503 (i.e., can be completed) by the same patch die 158 used to cut the patches 502. In such embodiments, the patch die 158 can include a two-level die having a first level configured to cut the patches 502 by cutting the adhesive laminate 532 up to the first web 548, without cutting through the first web 548 (i.e., the release liner 534); and a second level configured to cut the remaining portion of the tabs 503 (e.g., the leading edge 524) by cutting through the first web 548. However, as shown in FIGS. 9G and 9H, at least a portion of each patch 502 is still adhered to an uncut portion of the first web 548 (i.e., the release liner 534), so that the patches 502 and tabs 503 are maintained in place on the web. This is similar to the patch cutting process described above with respect to FIG. 3G, except that in this method, the leading edge 524 of each tab 503 is at the same longitudinal position as the leading edge 516 of the patch 502 that overlaps the tab 503. This allows the patches 502 to abut longitudinally, minimizing waste, such that the leading edge 524 of each tab 503 is also at the same longitudinal position as the trailing edge 520 of a downstream patch 502.

The ribbon guide 162 (see FIG. 2) can then be used to laterally separate (i.e., spread) the ribbons 554 of the first article 560 (see position H of FIG. 2 and FIG. 9H). The process represented by positions I-L of FIG. 2 can then be substantially the same as that described above with respect to FIGS. 3I-L. Namely, a second web 572 (see position J of FIG. 2 and FIG. 9J) can be provided, and the patches 502 and tabs 503 can be transferred from the first web 548 of the first article 560 onto the second web 572 to form a second article 570 (see position K of FIG. 2 and FIG. 9K), and the non-tab weed 576 of each ribbon 554 from the first web 548 of the first article 560 can be removed (see position I of FIG. 2 and FIG. 9I).

Figure 9J:
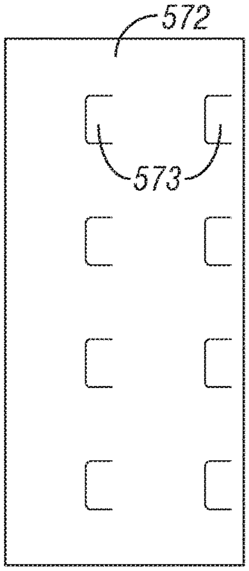

As shown in FIG. 9J, in some embodiments, the second web 572 can be provided with pre-cut longitudinally-spaced (and optionally also laterally spaced in embodiments employing multiple longitudinal ribbons 554) tabs 573 that can be spaced apart and positioned in the second web 572, such that they will each underlie at least a portion (e.g., a leading portion 522) of a tab 503 when the patches 502 and tabs 503 are transferred onto the second web 572. Such tabs 573 in the second web 572 can be used in a resulting adhesive patch assembly 500 (see FIG. 9L) to facilitate lifting the leading portion 522 (including the leading edge 524) of the tab 503 and a leading portion 514 (including the leading edge 516) of the patch 502 from a release liner 504 by pushing on the release liner tab 573 from a bottom side of the release liner 504 to push the tab 503 up off of the opposite top side of the release liner 504.

Figure 9K:
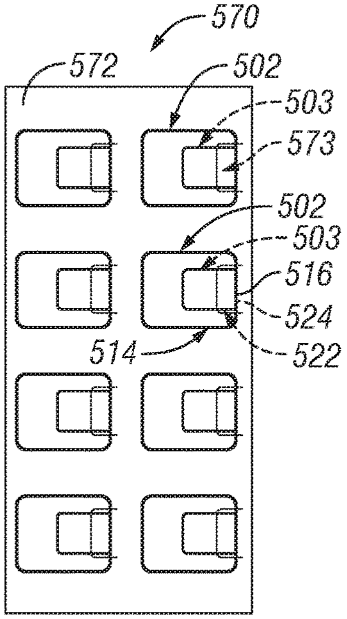
Figure 9L:
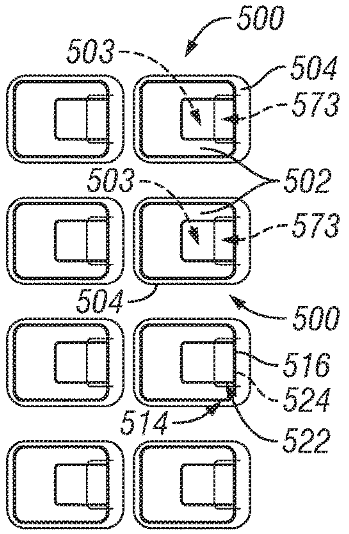

As shown in FIG. 9K, the second article 570 includes the patches 502 and the tabs 503 longitudinally spaced (and optionally, also laterally spaced if multiple ribbons 554 were employed) on the second web 572. As shown at position L of FIG. 2 and FIG. 9L, the second web 572 can then be cut around each set of patch 502 and tab 503 to form adhesive patch assemblies 500 of the present disclosure, including individual release liners 504.

The same relative motion between the second web 572 and the first web 548 (i.e., the first article 560) as described above can be used in the method of FIGS. 9A-9L, such that the relatively higher speed (i.e., no matter how it is achieved) of the second web 572 relative to the first web 548 causes a leading portion 514 (including the leading edge 516) of each patch 502 and a leading portion 522 (including the leading edge 524) of each tab 503 to be pulled by the second web 572 to transfer the patch 502 and the tab 503 from the first web 548 of the first article 560 to form the second article 570.

In some embodiments, the adhesive laminate patches prepared may comprise a drug. Suitable transdermal drug delivery devices include gelled or liquid reservoirs, such as in U.S. Pat. No. 4,834,979 (Gale), so-called "reservoir" patches; devices containing matrix reservoirs attached to the skin by an adjacent adhesive layer, such as in U.S. Pat. No. 6,004,578 (Lee, et al.), so-called "matrix" patches; and devices containing pressure-sensitive adhesive reservoirs, such as in U.S. Pat. No. 6,365,178 (Venkateshwaran et al.), U.S. Pat. No. 6,024,976 (Miranda et al.), and U.S. Pat. No. 6,149,935 (Chiang et al.), so-called "drug-in-adhesive" patches, the disclosures of which are incorporated herein by reference. The term reservoir is used herein to describe a portion of the patch which houses a drug and as described above may be liquid, solid, adhesive, or any other suitable form.

The length of time that a patch of the present disclosure remains in a delivering relationship is typically an extended time, for example, from about 12 hours to about 14 days. In certain embodiments, the length of time that the reservoir remains in a delivering relationship is about 1 day (i.e., daily dosing), about 3 to 4 days (bi-weekly dosing), or about 7 days (weekly dosing).

In some embodiments, the reservoir may contain other additives or excipients in addition to the pharmaceutically active agent. Such additives include pharmaceutically acceptable materials that may be used as skin penetration enhancers (i.e., substances that increase the permeation rate of a drug across or into the skin) or solubilizers (i.e., substances that effectively solubilize a drug) in transdermal drug delivery systems. Suitable materials used as skin permeation enhancers include $C_8$-$C_{20}$ fatty acids such as isostearic acid, octanoic acid, and oleic acid; $C_8$-$C_{20}$ fatty alcohols such as oleyl alcohol and lauryl alcohol; lower alkyl esters of $C_8$-$C_{20}$ fatty acids such as ethyl oleate, isopropyl myristate, butyl stearate, and methyl laurate; di(lower) alkyl esters of $C_6$-$C_8$ diacids such as diisopropyl adipate; monoglycerides of $C_8$-$C_{20}$ fatty acids such as glyceryl monolaurate; tetraglycol (tetrahydrofurfuryl alcohol polyethylene glycol ether); tetraethylene glycol (ethanol,2,2'-(oxybis(ethylenoxy))diglycol); $C_6$-$C_{20}$ alkyl pyrrolidone carboxylates; polyethylene glycol; propylene glycol; 2-(2-ethoxyethoxy) ethanol; diethylene glycol monomethyl ether; N,N-dimethyldodecylamine-N-oxide and combinations of the foregoing. Alkylaryl ethers of polyethylene oxide, polyethylene oxide monomethyl ethers, polyethylene oxide dimethyl ethers, glycerol, and N-methyl pyrrolidone are also suitable. The terpenes are another useful class of pharmaceutical excipients, including pinene, d-limonene, carene, terpineol, terpinen-4-ol, carveol, carvone, pulegone, piperitone, menthone, menthol, neomenthol, thymol, camphor, borneol, citral, ionone, and cineole, alone or in any combination. Examples of other additives include tackifiers, plasticizers, and anti-oxidants.

Exemplary pharmaceutically active agents (also referred to as "drugs") that can be included in the reservoir are capable of local or systemic effect when administered to the skin. Some examples include clonidine, estradiol, nicotine, nitroglycerine, scopolamine, and fentanyl, which are commercially available in the form of transdermal devices. Other examples include antiinflammatory drugs, both steroidal (e.g., hydrocortisone, prednisolone, triamcinolone) and non-steroidal (e.g., naproxen, piroxicam); bacteriostatic agents (e.g., chlorhexidine, hexylresorcinol); antibacterials (e.g., penicillins such as penicillin V, cephalosporins such as cephalexin, erythromycin, tetracycline, gentamycin, sulfathiazole, nitrofurantoin, and quinolones such as norfloxacin, flumequine, and ibafloxacin); antiprotazoals (e.g., metronidazole); antifungals (e.g., nystatin); coronary vasodilators; calcium channel blockers (e.g., nifedipine, diltiazem); bronchodilators (e.g., theophylline, pirbuterol, salmeterol, isoproterenol); enzyme inhibitors such as collagenase inhibitors, protease inhibitors, elastase inhibitors, lipoxygenase inhibitors (e.g., A64077), and angiotensin converting enzyme inhibitors (e.g., captopril, lisinopril); other antihypertensives (e.g., propranolol); leukotriene antagonists (e.g., ICI204,219); anti-ulceratives such as H2 antagonists; steroidal hormones (e.g., progesterone, testosterone, estradiol); antiviral s and/or immunomodulators (e.g., 1-isobutyl-1H-imidazo[4,5-c]quinolin-4-amine, 1-(2-hydroxy-2-methylpropyl)-1H-imidazo[4,5-c]quinolin-4-amine, and acyclovir); local anesthetics (e.g., benzocaine, propofol); cardiotonics (e.g., digitalis, digoxin); antitussives (e.g., codeine, dextromethorphan); antihistamines (e.g., diphenhydramine, chlorpheniramine, terfenadine); narcotic analgesics (e.g., morphine, buprenorphine); peptide hormones (e.g., human or animal growth hormones, LHRH); cardioactive products such as atriopeptides; proteinaceous products (e.g., insulin); enzymes (e.g., anti-plaque enzymes, lysozyme, dextranase); antinauseants; anticonvulsants (e.g., carbamazine); immunosuppressives (e.g., cyclosporine); psychotherapeutics (e.g., diazepam); sedatives (e.g., phenobarbital); anticoagulants (e.g., heparin); analgesics (e.g., acetaminophen); antimigraine agents (e.g., ergotamine, melatonin, sumatripan); antiarrhythmic agents (e.g., flecainide); antiemetics (e.g., metaclopromide, ondansetron); anticancer agents (e.g., methotrexate); neurologic agents such as anxiolytic drugs; hemostatics; anti-obesity agents; and the like, as well as pharmaceutically acceptable salts and esters thereof. The amount of drug that constitutes a therapeutically effective amount can be readily determined by those skilled in the art with due consideration of the particular drug, the particular carrier, and the desired therapeutic effect. Generally, the device will be in the form of a patch with a size suitable to deliver a selected amount of drug through the skin.

Generally, patches of the present disclosure can have a surface area greater than about 1 $cm^2$, and sometimes greater than about 5 $cm^2$. Generally, the patches can have a surface area of less than about 100 $cm^2$, and sometimes less than about 40 $cm^2$. In some embodiments, patches (or adhesive patch assemblies) of the present disclosure may be packaged individually in a foil-lined pouch for storage. In some embodiments, patches (or adhesive patch assemblies) of the present disclosure may alternatively be provided in a rolled or stacked form suitable for use with a dispensing apparatus.

In some embodiments, it may be desirable to have one or more cuts or splits in the release liner to assist in removal of the patch from the liner.

In some embodiments, the release liner has a larger area than the adhesive portion of the patch, thereby providing an extended liner. The distance that the release liner extends beyond the margins of the adhesive portion of the patch can be any suitable distance, and may depend upon a number of factors including, for example, the size of the adhesive portion of the patch, the types of adhesive, backing, and liner employed, and the patient population using the patch. In some embodiments, the area of the release liner may be less than or equal to about 10 times, sometimes less than or equal to about 2.5 times, and often less than or equal to 1.5 times the area of the adhesive portion of the device. The distance that the liner extends may be uniform around the circumference of the patch or it may vary, for example, by providing a smaller circular patch on a square-shaped extended liner.

Each embodiment shown in the figures is illustrated as a separate embodiment for clarity in illustrating a variety of features of the methods and adhesive patch assemblies of the present disclosure. However, it should be understood that any combination of elements and features of any of the embodiments illustrated in the figures and described herein can be employed in the methods and adhesive patch assemblies of the present disclosure.

The following embodiments are intended to be illustrative of the present disclosure and not limiting.

EMBODIMENTS

1. A method of handling an adhesive laminate patches, the method comprising:
   - providing a first article comprising a plurality of disconnected adhesive laminate patches adhered to a first web, wherein each patch is aligned over and adhered to a tab in the first web, such that a leading edge of each tab is located adjacent a leading edge of each patch;
   - providing a first supporting structure and a second supporting structure positioned adjacent the first supporting structure, wherein the second supporting structure and the first supporting structure are separated by a gap;
   - leading a second web over the second supporting structure, wherein the second web has a release surface, and wherein the second web is oriented such that the release surface of the second web faces the first supporting structure;
   - passing the first article over the first supporting structure to cause a leading portion of a first tab and a leading portion of a first patch aligned over the first tab to lift off of the first web together in such a way that the leading portion of the first patch is supported by the first tab and extends across the gap between the first supporting structure and the second supporting structure;
   - adhering the leading portion of the first patch to the second web on the second supporting structure; and
   - advancing the second web on the second supporting structure to transfer the first patch from the first web to the second web to form a second article comprising a plurality of patches aligned over tabs on the second web, wherein the patches are spaced apart longitudinally on the second web.

2. The method of embodiment 1, wherein providing a first article comprising a plurality of disconnected adhesive laminate patches adhered to a first web includes:
   - providing an adhesive laminate on a third supporting structure in such a way that the adhesive of the adhesive laminate faces away from the third supporting structure;
   - providing the first web comprising a plurality of partially-cut tabs arranged along a machine direction of the first web, the first web having a release surface;
   - providing a fourth supporting structure adjacent the third supporting structure;

leading the first web over the fourth supporting structure, wherein the first web is oriented such that the release surface of the first web faces the third supporting structure;

transferring the adhesive laminate from the third supporting structure onto the first web on the fourth supporting structure to form a precursor article comprising the adhesive laminate adhered to the release surface of the first web; and cutting the adhesive laminate of the precursor article to form the plurality of disconnected adhesive laminate patches adhered to the first web.

3. The method of embodiment 2, wherein cutting the adhesive laminate includes forming a non-patch weed adhered to the first web; and further comprising:

removing the non-patch weed from the adhesive laminate patches and the first web to form the first article comprising the plurality of disconnected adhesive laminate patches adhered to the first web.

4. The method of embodiment 2 or 3, wherein providing an adhesive laminate on a third supporting structure in such a way that the adhesive of the adhesive laminate faces away from the third supporting structure includes:

providing the adhesive laminate releasably adhered to a starter web;

separating the adhesive laminate from the starter web and leading the adhesive laminate over the third supporting structure; and wherein providing a first web comprising a plurality of partially-cut tabs includes:

cutting the starter web while it is separated from the adhesive laminate to form the plurality of partially-cut tabs.

5. The method of embodiment 4, wherein cutting the first web includes forming at least one longitudinal cut to form a plurality of ribbons, wherein each ribbon includes a plurality of partially-cut tabs arranged along the ribbon in the machine direction.

6. The method of embodiment 2 or 3, further comprising:

providing the adhesive laminate releasably adhered to a starter web; and separating the adhesive laminate from the starter web and leading the adhesive laminate over the first supporting structure.

7. The method of any of embodiments 2-6, wherein providing the first web comprising a plurality of partially-cut tabs includes providing the first web comprising at least one longitudinal cut to form a plurality of ribbons, wherein each ribbon includes a plurality of partially-cut tabs arranged along the ribbon in the machine direction.

8. The method of embodiment 7, wherein the precursor article and the first article each include a plurality of ribbons, and wherein each ribbon of the first article includes a plurality of disconnected adhesive laminate patches on the first web.

9. The method of embodiment 8, further comprising separating the plurality of ribbons of the first article laterally apart prior to passing the first article over the first supporting structure.

10. The method of any of embodiments 2-9, wherein cutting the adhesive laminate of the precursor article to form a plurality of disconnected adhesive laminate patches adhered to the first web occurs as the adhesive laminate is being transferred from the third supporting structure to the fourth supporting structure.

11. The method of any of embodiments 2-10, wherein adhering the adhesive laminate to the first web occurs on the fourth supporting structure as the adhesive laminate is transferred to the fourth supporting structure.

12. The method of any of embodiments 2-11, wherein the plurality of partially-cut tabs in the first web are spaced from one another in the machine direction.

13. The method of any of embodiments 2-12, wherein the plurality of partially-cut tabs in the first web are spaced from one another in a cross-machine direction.

14. The method of any of embodiments 2-13, wherein cutting the adhesive laminate of the precursor article to form a plurality of disconnected adhesive laminate patches also finishes cutting out the plurality of partially-cut tabs in the first web.

15. The method of embodiment 14, wherein cutting the adhesive laminate of the precursor article and finishing cutting out the plurality of partially-cut tabs in the first web is performed using a two-level die.

16. The method of any of embodiments 2-15, wherein each partially-cut tab is coupled to the first web via at least one tie point.

17. The method of embodiment 16, wherein each partially-cut tab is configured to be separated from the first web by fracturing the at least one tie point.

18. The method of embodiment 17, wherein each partially-cut tab is configured to be separated from the first web by fracturing the at least one tie point when the leading portion of the first tab and the leading portion of the first patch lift off of the first web and the leading portion of the first patch is adhered to the second web.

19. The method of any of embodiments 1-18, wherein each tab is more rigid than its aligned adhesive laminate patch.

20. The method of any of any of embodiments 1-19, wherein the first article includes the plurality of adhesive laminate patches spaced longitudinally from one another on the first web.

21. The method of any of embodiments 1-20, wherein the first article includes the plurality of adhesive laminate patches positioned directly adjacent one another on the first web in the machine direction.

22. The method of any of embodiments 1-21, wherein the first article includes the plurality of adhesive laminate patches positioned directly adjacent one another on the first web in the cross-machine direction.

23. The method of any of embodiments 1-22, wherein the leading portion of each tab includes a leading edge, and wherein the leading edge of each tab in the first article is located directly adjacent a leading edge of an adhesive laminate patch and the trailing edge of a downstream adhesive laminate patch.

24. The method of any of embodiments 1-23, wherein the leading portion of each tab includes a leading edge, and wherein the leading edge of each tab in the second article is located downstream of a leading edge of its aligned adhesive laminate patch.

25. The method of any of embodiments 1-24, wherein a lateral edge of each adhesive laminate patch in the first article is located directly adjacent a lateral edge of another adhesive laminate patch.

26. The method of any of embodiments 1-25, wherein a leading edge of each adhesive laminate patch in the first article is located directly adjacent a trailing edge of another adhesive laminate patch.

27. The method of any of embodiments 1-26, wherein the first web is moved in an intermittent motion over the first supporting structure.

28. The method of any of embodiments 1-27, wherein the second web is accelerated over the second supporting structure relative to the first web on the first supporting structure.

29. The method of any of embodiments 1-28, further comprising cutting the second web around each adhesive laminate patch to form a release liner for each adhesive laminate patch, wherein the release liner of each patch extends beyond the patch in all directions.

30. The method of any of embodiments 1-29, further comprising cutting the second web around each of the plurality of adhesive laminate patches to form a plurality of adhesive patch assemblies, the second web forming a release liner.

31. The method of embodiment 30, wherein the release liner includes an overlay liner.

32. The method of embodiment 31, wherein the second article includes the plurality of adhesive laminate patches longitudinally-spaced on the second web, such that the second web can be used to form a release liner comprising an overlay liner.

33. The method of any of embodiments 30-32, further comprising applying an adhesive laminate patch to a surface of interest by:

lifting the tab from the release liner and using the tab to peel the adhesive laminate patch from the release liner;

adhering a trailing portion of the adhesive laminate patch to the surface of interest;

exposing the tab; and continuing to adhere the adhesive laminate patch to the desired surface while removing the tab from the adhesive of the adhesive laminate patch until the adhesive laminate patch is adhered to the desired surface and the tab has been removed from the adhesive laminate patch.

34. The method of embodiment 33, wherein exposing the tab includes folding a leading portion of the patch back over the adhered trailing portion of the patch.

35. The method of embodiment 33 or 34, wherein exposing the tab includes exposing a trailing edge of the tab, and wherein continuing to adhere the adhesive laminate patch includes pushing the tab in the direction of the trailing edge of the tab.

36. The method of embodiment 35, wherein continuing to adhere the adhesive laminate patch includes laying down the patch from the trailing portion to a leading portion of the patch.

37. A method of handling adhesive laminate patches, the method comprising:

providing an adhesive laminate on a first supporting structure in such a way that the adhesive of the adhesive laminate faces away from the first supporting structure;

providing a first web comprising a plurality of partially-cut tabs arranged along a machine direction of the first web, the first web having a release surface;

providing a second supporting structure adjacent the first supporting structure;

leading the first web over the second supporting structure, wherein the first web is oriented such that the release surface of the first web faces the first supporting structure;

transferring the adhesive laminate from the first supporting structure onto the first web on the second supporting structure to form a precursor article comprising the adhesive laminate adhered to the release surface of the first web;

cutting the adhesive laminate of the precursor article to form a plurality of disconnected adhesive laminate patches and a non-patch weed adhered to the first web, wherein each patch is aligned over and adhered to a tab in the first web, such that a leading edge of each tab is located adjacent a leading edge of each patch;

separating the non-patch weed from the precursor article to form a first article comprising the plurality of disconnected adhesive laminate patches adhered to the first web;

providing a third supporting structure located downstream of the second supporting structure;

providing a fourth supporting structure adjacent the third supporting structure, wherein the fourth supporting structure and the third supporting structure are separated by a gap;

leading a second web over the fourth supporting structure, wherein the second web has a release surface, and wherein the second web is oriented such that the release surface of the second web faces the third supporting structure;

passing the first article over the third supporting structure to cause a leading portion of a first tab and a leading portion of a first patch aligned over the first tab to lift off of the first web together in such a way that the leading portion of the first patch is supported by the first tab and extends across the gap between the third supporting structure and the fourth supporting structure;

adhering the leading portion of the first patch to the second web on the fourth supporting structure; and advancing the second web on the fourth supporting structure to transfer the first patch from the first web to the second web to form a second article comprising a plurality of patches on the second web, wherein the patches are spaced apart longitudinally on the second web.

Some embodiments of the present disclosure further include a combination of embodiment 37 with any one or more of the features of embodiments 3-36.

It is to be understood that the invention is not limited in its application to the details of construction and the arrangement of components set forth in the above description or illustrated in the accompanying drawings. The invention is capable of other embodiments and of being practiced or of being carried out in various ways. Also, it is to be understood that the phraseology and terminology used herein is for the purpose of description and should not be regarded as limiting. It is to be further understood that other embodiments may be utilized, and structural or logical changes may be made without departing from the scope of the present disclosure.

The embodiments described above and illustrated in the figures are presented by way of example only and are not intended as a limitation upon the concepts and principles of the present disclosure. As such, it will be appreciated by one having ordinary skill in the art that various changes in the elements and their configuration and arrangement are possible without departing from the spirit and scope of the present disclosure.

All references and publications cited herein are expressly incorporated herein by reference in their entirety into this disclosure.

Various features and aspects of the present disclosure are set forth in the following claims.

What is claimed is:

1. A method of handling adhesive laminate patches, the method comprising:

providing a first article comprising a plurality of disconnected adhesive laminate patches adhered to a first web, wherein each patch is aligned over and adhered to a tab in the first web, such that a leading edge of each tab is located adjacent a leading edge of each patch;

providing a first supporting structure and a second supporting structure positioned adjacent the first supporting structure, wherein the second supporting structure and the first supporting structure are separated by a gap;

leading a second web over the second supporting structure, wherein the second web has a release surface, and wherein the second web is oriented such that the release surface of the second web faces the first supporting structure;

passing the first article over the first supporting structure to cause a leading portion of a first tab and a leading portion of a first patch aligned over the first tab to lift off of the first web together in such a way that the leading portion of the first patch is supported by the first tab and extends across the gap between the first supporting structure and the second supporting structure;

adhering the leading portion of the first patch to the second web on the second supporting structure; and advancing the second web on the second supporting structure to transfer the first patch from the first web to the second web to form a second article comprising a plurality of patches aligned over tabs on the second web, wherein the patches are spaced apart longitudinally on the second web.

2. The method of claim 1, wherein providing a first article comprising a plurality of disconnected adhesive laminate patches adhered to a first web includes:

providing an adhesive laminate on a third supporting structure in such a way that the adhesive of the adhesive laminate faces away from the third supporting structure;

providing the first web comprising a plurality of partially-cut tabs arranged along a machine direction of the first web, the first web having a release surface;

providing a fourth supporting structure adjacent the third supporting structure;

leading the first web over the fourth supporting structure, wherein the first web is oriented such that the release surface of the first web faces the third supporting structure;

transferring the adhesive laminate from the third supporting structure onto the first web on the fourth supporting structure to form a precursor article comprising the adhesive laminate adhered to the release surface of the first web; and cutting the adhesive laminate of the precursor article to form the plurality of disconnected adhesive laminate patches adhered to the first web.

3. The method of claim 2, wherein cutting the adhesive laminate includes forming a non-patch weed adhered to the first web; and further comprising:

removing the non-patch weed from the adhesive laminate patches and the first web to form the first article comprising the plurality of disconnected adhesive laminate patches adhered to the first web.

4. The method of claim 2, wherein providing an adhesive laminate on a third supporting structure in such a way that the adhesive of the adhesive laminate faces away from the third supporting structure includes:

providing the adhesive laminate releasably adhered to a starter web;

separating the adhesive laminate from the starter web and leading the adhesive laminate over the third supporting structure; and wherein providing a first web comprising a plurality of partially-cut tabs includes:

cutting the starter web while it is separated from the adhesive laminate to form the plurality of partially-cut tabs.

5. The method of claim 4, further comprising forming at least one longitudinal cut in the first web to form a plurality of ribbons, wherein each ribbon includes a plurality of partially-cut tabs arranged along the ribbon in the machine direction.

6. The method of claim 2, further comprising:

providing the adhesive laminate releasably adhered to a starter web; and separating the adhesive laminate from the starter web and leading the adhesive laminate over the first supporting structure.

7. The method of claim 2, wherein providing the first web comprising a plurality of partially-cut tabs includes providing the first web comprising at least one longitudinal cut to form a plurality of ribbons, wherein each ribbon includes a plurality of partially-cut tabs arranged along the ribbon in the machine direction.

8. The method of claim 2, wherein the plurality of partially-cut tabs in the first web are spaced from one another in at least one of the machine direction and a cross-machine direction.

9. The method of claim 2, wherein cutting the adhesive laminate of the precursor article to form a plurality of disconnected adhesive laminate patches also finishes cutting out the plurality of partially-cut tabs in the first web.

10. The method of claim 2, wherein each partially-cut tab is coupled to the first web via at least one tie point.

11. The method of claim 2, wherein each tab is more rigid than its aligned adhesive laminate patch.

12. The method of claim 2, wherein the first article includes the plurality of adhesive laminate patches spaced longitudinally from one another on the first web.

13. The method of claim 2, wherein the first article includes the plurality of adhesive laminate patches positioned directly adjacent one another on the first web in at least one of the machine direction and a cross-machine direction.

14. The method of claim 1, further comprising cutting the second web around each of the plurality of adhesive laminate patches to form a plurality of adhesive patch assemblies, the second web forming a release liner.

15. The method of claim 14, wherein the release liner includes an overlay liner.

* * * * *